US009023059B2

(12) United States Patent  (10) Patent No.: US 9,023,059 B2
Loushin et al.  (45) Date of Patent: May 5, 2015

(54) VENTILATION DEVICE AND INSERTION SYSTEM THEREFOR

(75) Inventors: Michael K. H. Loushin, Shoreview, MN (US); Keith J. Leland, Medina, MN (US); Jaydeep Yeshwant Kokate, Plymouth, MN (US)

(73) Assignee: Preceptis Medical, Inc., Plymouth, MN (US)

( * ) Notice: Subject to any disclaimer, the term of this patent is extended or adjusted under 35 U.S.C. 154(b) by 1197 days.

(21) Appl. No.: 12/389,552

(22) Filed: Feb. 20, 2009

(65) Prior Publication Data

US 2009/0209972 A1   Aug. 20, 2009

Related U.S. Application Data

(60) Provisional application No. 61/030,068, filed on Feb. 20, 2008.

(51) Int. Cl.
| | |
|---|---|
| *A61F 11/00* | (2006.01) |
| *A61M 27/00* | (2006.01) |
| *A61M 31/00* | (2006.01) |
| *A61B 17/34* | (2006.01) |
| *A61B 17/00* | (2006.01) |

(Continued)

(52) U.S. Cl.
CPC .............. *A61F 11/002* (2013.01); *A61M 27/00* (2013.01); *A61M 31/00* (2013.01); *A61B 17/3468* (2013.01); *A61B 2017/00787* (2013.01); *A61M 25/01* (2013.01); *A61M 25/0662* (2013.01)

(58) Field of Classification Search
USPC ...................... 606/109, 108, 185; 604/8, 244; 623/6.11, 6.12
See application file for complete search history.

(56) References Cited

U.S. PATENT DOCUMENTS

| 3,530,860 A | 9/1970 | Majoros |
| 3,662,754 A | 5/1972 | Halloran |

(Continued)

FOREIGN PATENT DOCUMENTS

| CN | 101068516 | 11/2007 |
| GB | 2437708 A | 11/2007 |

(Continued)

OTHER PUBLICATIONS

Communication dated Dec. 4, 2012 in Chinese application No. 200980113954.0, filed Feb. 20, 2009, with English translation attached, 7 pages.

(Continued)

*Primary Examiner* — Victor Nguyen
*Assistant Examiner* — Kevin Everage
(74) *Attorney, Agent, or Firm* — Leanne Taveggia Farrell; Westman, Champlin & Koehler, P.A.

(57) ABSTRACT

A ventilation device includes a hollow body having a main portion, at least one distal member coupled to a distal end of the main portion and at least one proximal member coupled to a proximal end of the main portion. The at least one distal member is formed of a shape memory material. The hollow body includes a deployed state for maintaining an opening in an anatomical structure and an undeployed state. The shape memory material forms the at least one distal member into a deployed position. The shape memory material is reversibly deformed from the deployed state into the undeployed state such that at least the distal member changes in shape to an undeployed position, while the main portion of the hollow body remains unchanged.

16 Claims, 16 Drawing Sheets

(51) Int. Cl.
*A61M 25/01* (2006.01)
*A61M 25/06* (2006.01)

(56) References Cited

U.S. PATENT DOCUMENTS

| | | |
|---|---|---|
| 3,807,409 A | 4/1974 | Paparella et al. |
| 3,871,380 A | 3/1975 | Heros |
| 3,888,258 A | 6/1975 | Akiyama |
| 3,897,786 A | 8/1975 | Garnett et al. |
| 3,913,584 A | 10/1975 | Walchle et al. |
| 3,948,271 A | 4/1976 | Akiyama |
| 4,174,716 A | 11/1979 | Treace |
| 4,334,538 A | 6/1982 | Juhn |
| 4,445,517 A | 5/1984 | Feild |
| 4,468,218 A | 8/1984 | Armstrong |
| 4,473,073 A | 9/1984 | Darnell |
| 4,580,568 A | 4/1986 | Gianturco |
| 4,695,275 A | 9/1987 | Bruce et al. |
| 4,744,792 A | 5/1988 | Sander et al. |
| 4,964,850 A | 10/1990 | Bouton et al. |
| 5,026,378 A | 6/1991 | Goldsmith, III |
| 5,053,040 A | 10/1991 | Goldsmith, III |
| 5,073,166 A | 12/1991 | Parks et al. |
| 5,139,502 A | 8/1992 | Berg et al. |
| 5,178,623 A | 1/1993 | Cinberg et al. |
| 5,207,685 A | 5/1993 | Cinberg et al. |
| 5,254,120 A | 10/1993 | Cinberg et al. |
| 5,466,239 A | 11/1995 | Cinberg et al. |
| 5,484,434 A | 1/1996 | Cartmell et al. |
| 5,496,329 A | 3/1996 | Reisinger |
| 5,566,094 A | 10/1996 | Kojuma et al. |
| 5,578,053 A | 11/1996 | Yoon |
| 5,601,568 A | 2/1997 | Chevillon et al. |
| 5,643,280 A | 7/1997 | Del Rio et al. |
| 5,645,584 A | 7/1997 | Suyama |
| 5,665,094 A | 9/1997 | Goldenberg |
| 5,693,065 A | 12/1997 | Rains, III |
| D389,915 S | 1/1998 | Emerson et al. |
| 5,709,677 A | 1/1998 | Slatkine |
| 5,711,309 A | 1/1998 | Goldenberg |
| 5,916,150 A | 6/1999 | Sillman |
| 5,976,151 A | 11/1999 | Siegbahn |
| 6,027,532 A | 2/2000 | Hobeika |
| D439,337 S | 3/2001 | Jones |
| 6,245,077 B1 | 6/2001 | East et al. |
| 6,258,067 B1 | 7/2001 | Hill |
| 6,292,702 B1 * | 9/2001 | King et al. ............... 607/116 |
| D453,833 S | 2/2002 | Hess |
| 6,361,526 B1 | 3/2002 | Reisdorf et al. |
| 6,390,975 B1 | 5/2002 | Walls et al. |
| 6,406,453 B1 | 6/2002 | Goode et al. |
| 6,443,970 B1 | 9/2002 | Schulze et al. |
| 6,527,780 B1 | 3/2003 | Wallace et al. |
| 6,692,455 B2 | 2/2004 | Goode et al. |
| 6,695,861 B1 | 2/2004 | Rosenberg et al. |
| D490,152 S | 5/2004 | Myall et al. |
| 6,730,056 B1 | 5/2004 | Ghaem et al. |
| 6,770,080 B2 | 8/2004 | Kaplan et al. |
| 6,776,797 B1 | 8/2004 | Blom et al. |
| 6,936,023 B2 | 8/2005 | Goode et al. |
| 6,939,494 B2 | 9/2005 | Goode et al. |
| D521,641 S | 5/2006 | Reschke et al. |
| D538,936 S | 3/2007 | Böhmel et al. |
| 7,235,099 B1 | 6/2007 | Duncavage et al. |
| 7,410,480 B2 | 8/2008 | Muni et al. |
| 7,419,497 B2 | 9/2008 | Muni et al. |
| 7,704,259 B2 | 4/2010 | Kaplan et al. |
| D619,579 S | 7/2010 | Flores Rodrigues Vieira |
| 7,879,033 B2 | 2/2011 | Sartor et al. |
| 8,052,693 B2 | 11/2011 | Shahoian |
| D664,657 S | 7/2012 | Vieira et al. |
| D673,676 S | 1/2013 | Goudreau et al. |
| 2002/0058899 A1 | 5/2002 | Goode et al. |
| 2003/0018291 A1 | 1/2003 | Hill et al. |
| 2005/0004520 A1 | 1/2005 | Lemoine et al. |
| 2005/0256450 A1 | 11/2005 | Palasis et al. |
| 2008/0051804 A1 | 2/2008 | Cottler et al. |
| 2008/0097295 A1 | 4/2008 | Makower et al. |
| 2008/0234708 A1 | 9/2008 | Houser et al. |
| 2008/0262468 A1 | 10/2008 | Clifford et al. |
| 2008/0262505 A1 | 10/2008 | Shahoian |
| 2008/0262508 A1 * | 10/2008 | Clifford et al. ............... 606/109 |
| 2008/0262509 A1 | 10/2008 | Clifford et al. |
| 2008/0262510 A1 | 10/2008 | Clifford |
| 2009/0275955 A1 | 11/2009 | Kutluhan |
| 2010/0256653 A1 | 10/2010 | Kaplan et al. |
| 2011/0288559 A1 | 11/2011 | Shahoian |
| 2012/0179187 A1 | 7/2012 | Loushin et al. |

FOREIGN PATENT DOCUMENTS

| | | |
|---|---|---|
| WO | 03057082 A1 | 7/2003 |
| WO | 2008131195 A2 | 10/2008 |
| WO | 2012094666 | 7/2012 |

OTHER PUBLICATIONS

Search Report and Written Opinion dated Apr. 25, 2012 from International Application No. PCT/US2012/020629, filed Jan. 9, 2012, 13 pages.

Extended European Search Report dated Aug. 25, 2011 issued in European patent application No. 09713274.0, filed Feb. 20, 2009, pp. 1-7.

Communication from European Patent Office dated Sep. 13, 2011 issued in European patent application No. 09713274.0, filed Feb. 20, 2009, 1 page.

Search Report and Written Opinion dated Oct. 1, 2009 from International application No. PCT/US2009/034648, filed Feb. 20, 2009.

Office Action dated Jul. 22, 2013 issued in Chinese Patent Application No. 200980113954.0 filed Feb. 20, 2009, with English translation attached, 9 pages.

Search Report and Written Opinion dated Sep. 18, 2013 issued in International Application No. PCT/US2013/045082, filed Jun. 11, 2013, 13 pages.

Pending U.S. Appl. No. 13/826,497, filed Mar. 14, 2013, entitled Insertion System for Deploying a Ventilation Device, 79 pages.

Pending U.S. Appl. No. 14/145,427, filed Oct. 3, 2013, entitled Stabilization System and Aspiration Device with Rapid Diagnostics, 51 pages.

Examination Report dated Jul. 18, 2013 issued in Australian Patent Application No. 2009215468 filed Feb. 20, 2009, 4 pages.

Office Action dated Jan. 28, 2014 issued in Chinese Patent Application No. 200980113954.0 filed Feb. 20, 2009, with English translation attached, 16 pages.

Office Action dated Jul. 11, 2014 issued in Chinese Patent Application No. 200980113954.0 filed Feb. 20, 2009, with English translation attached, 9 pages.

* cited by examiner

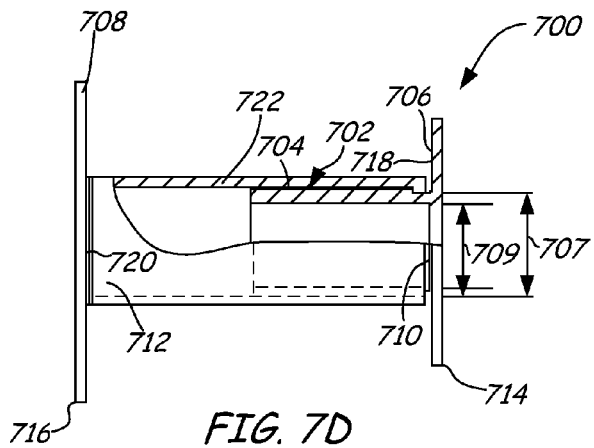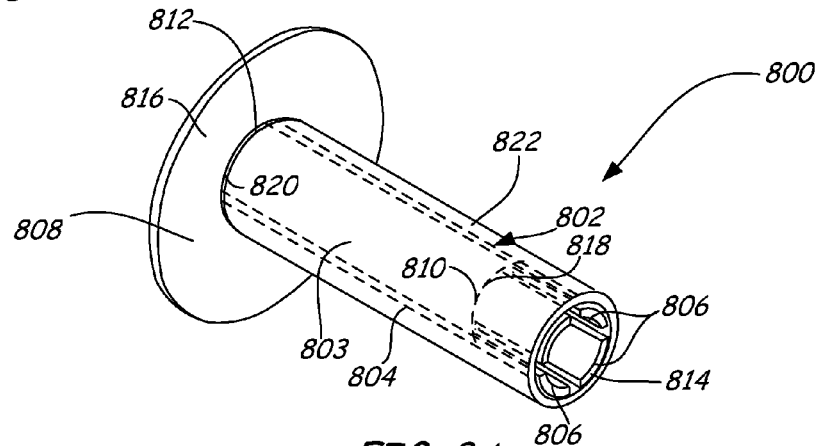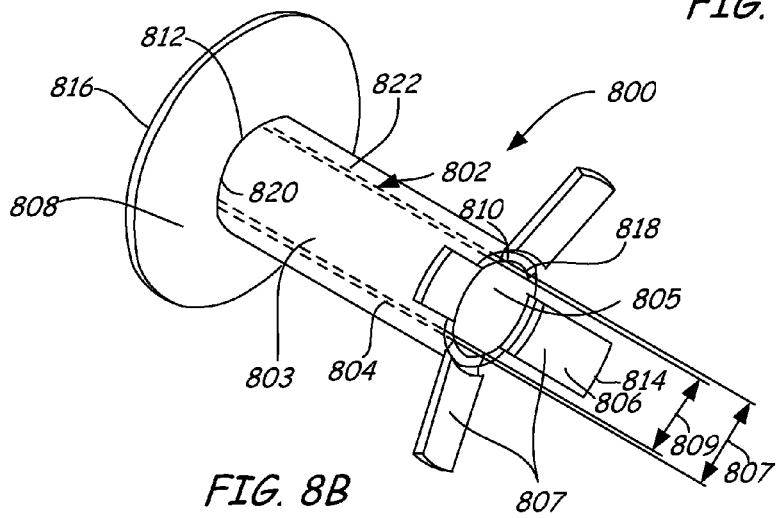

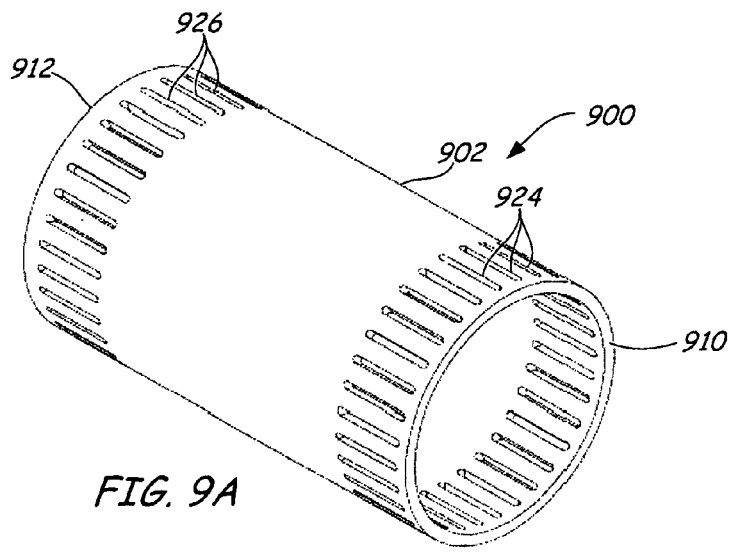
FIG. 9A
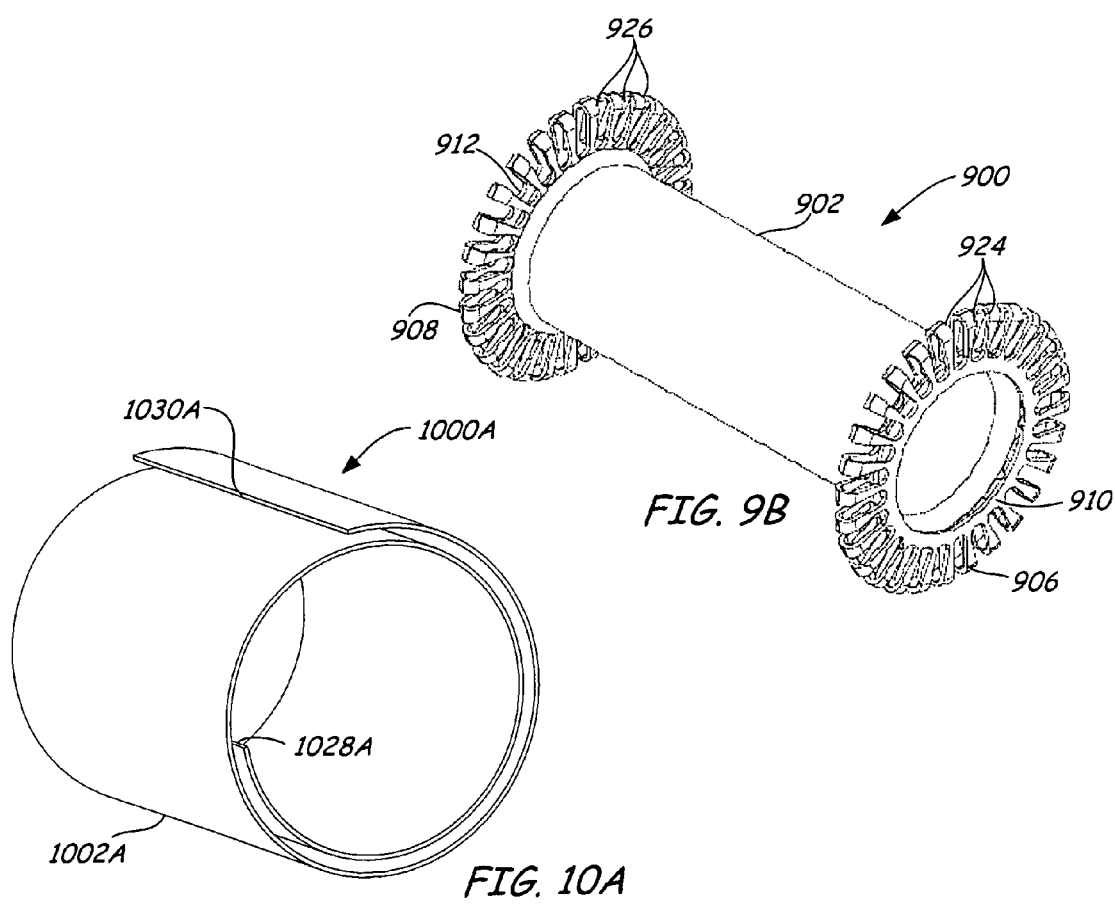
FIG. 9B
FIG. 10A

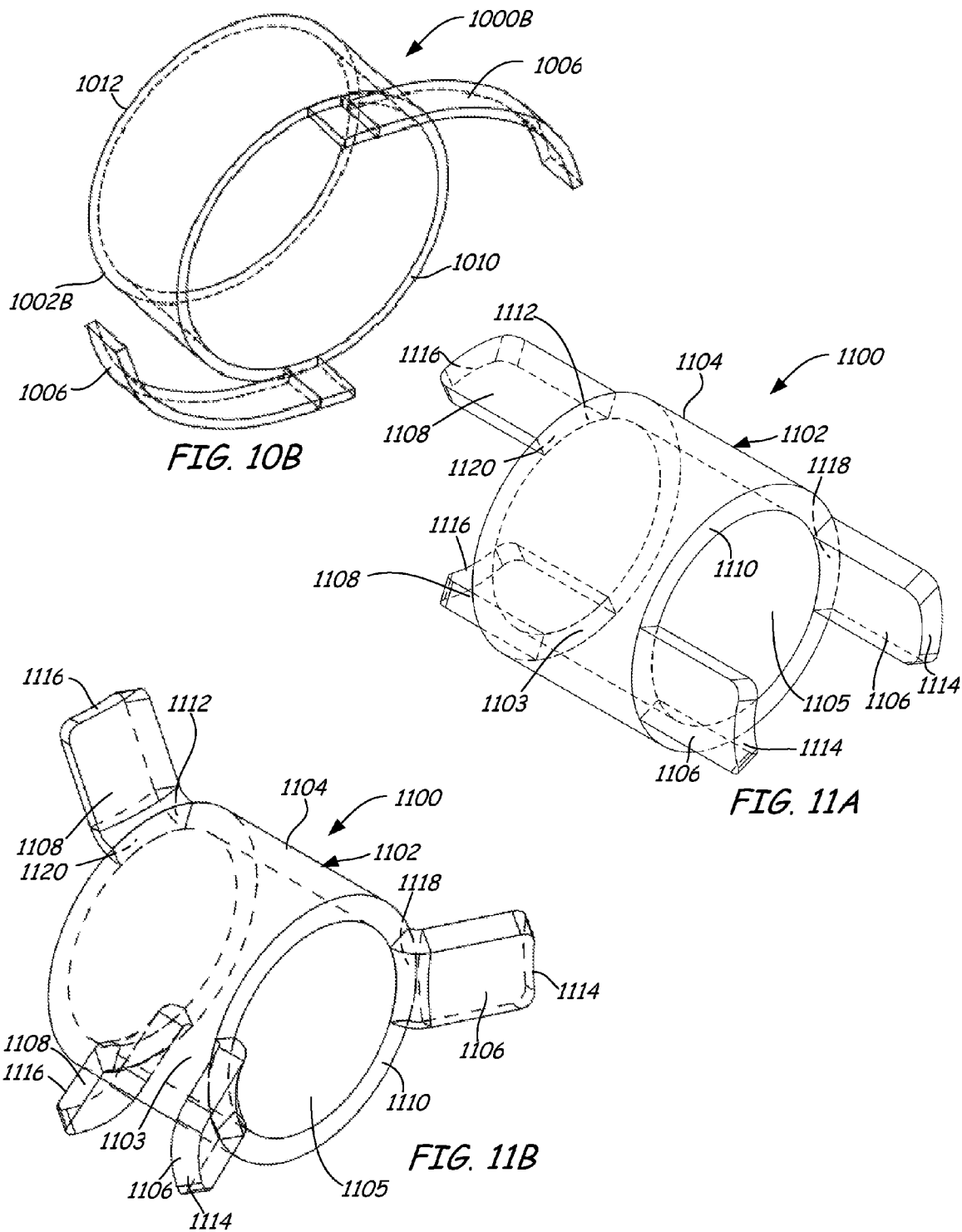

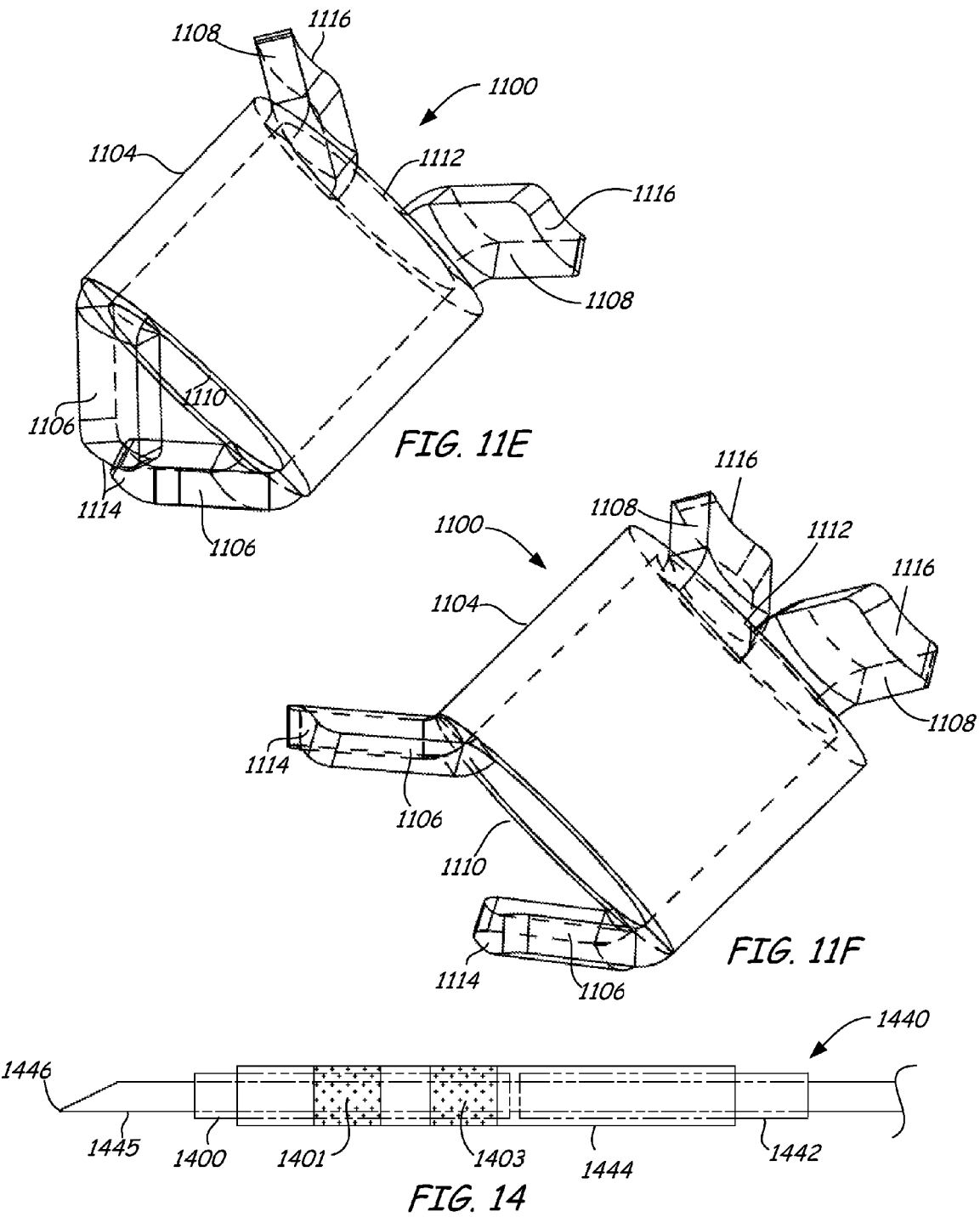

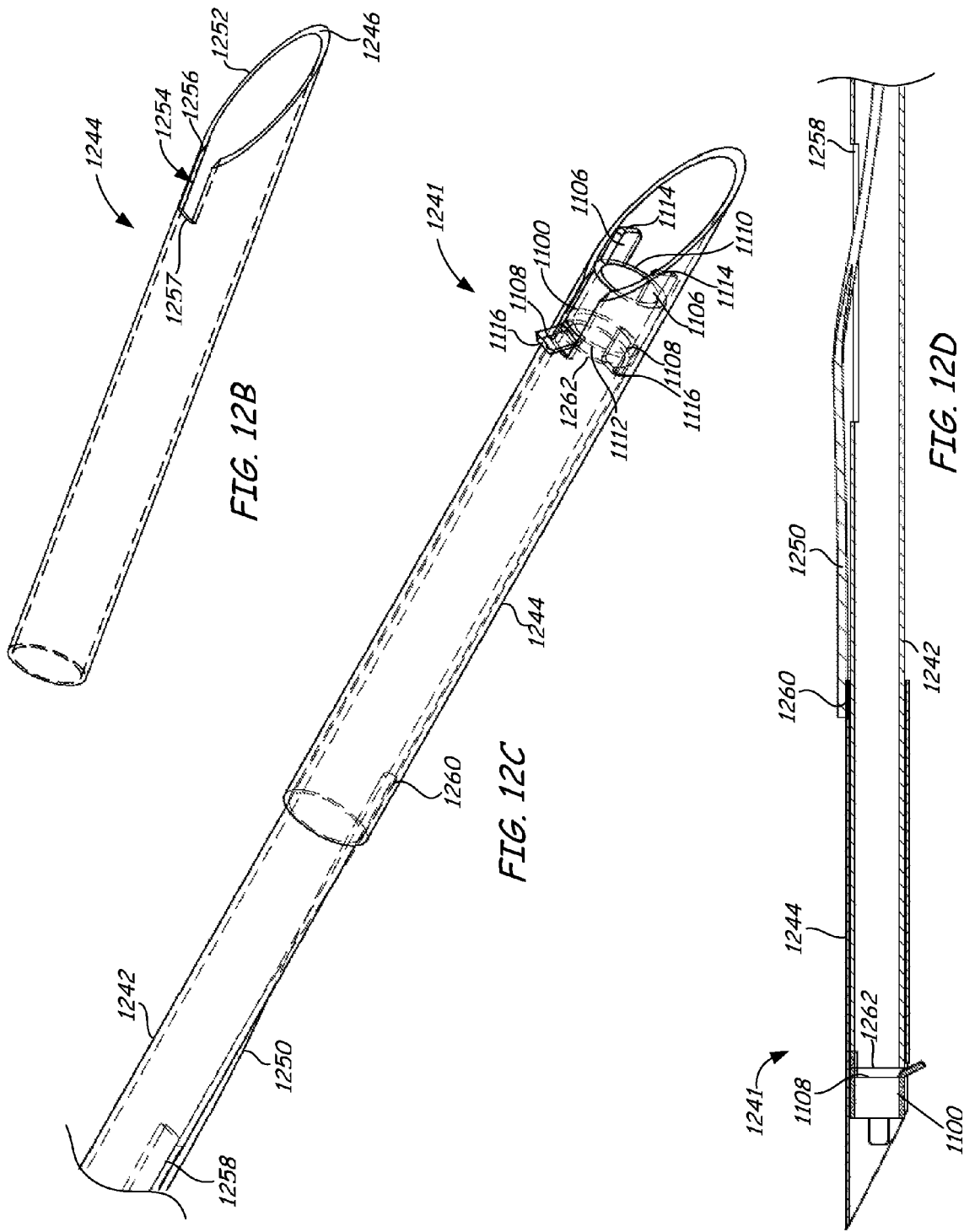

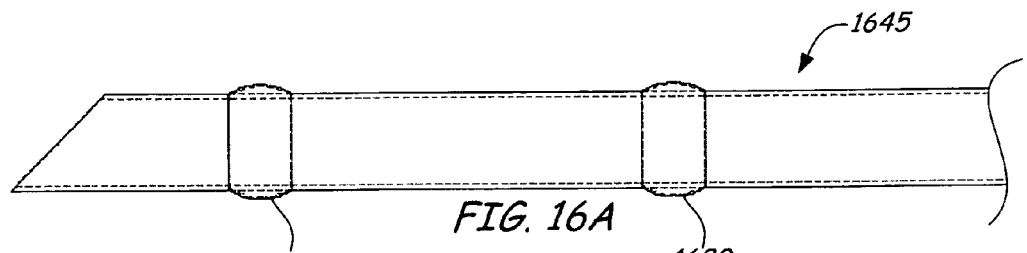
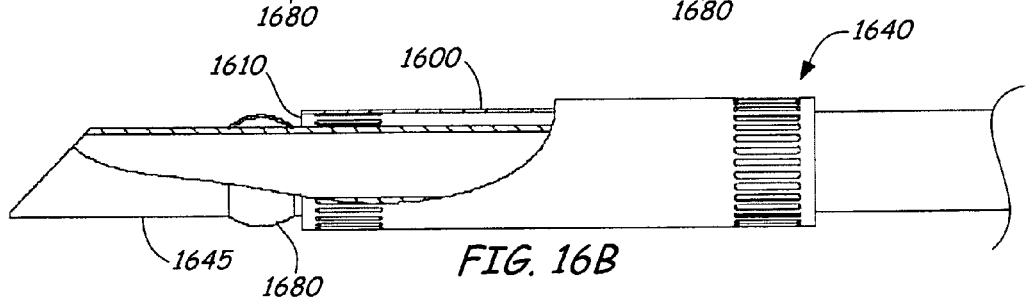
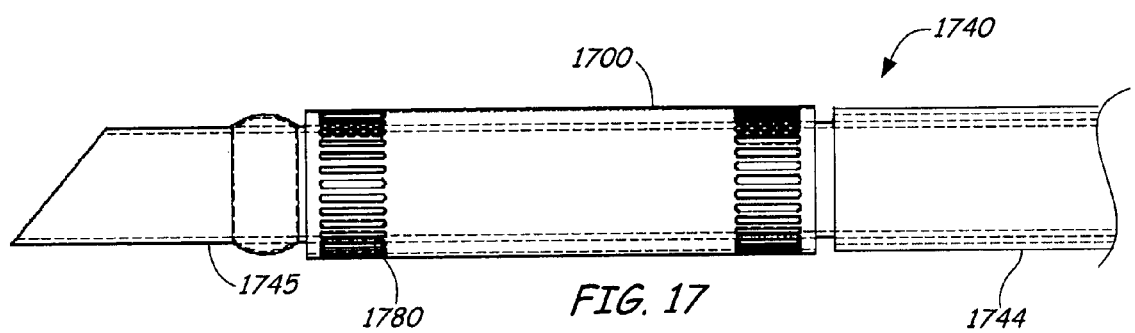
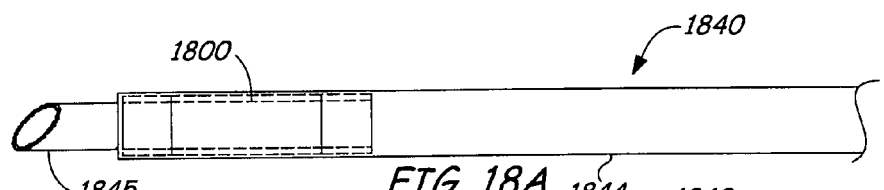
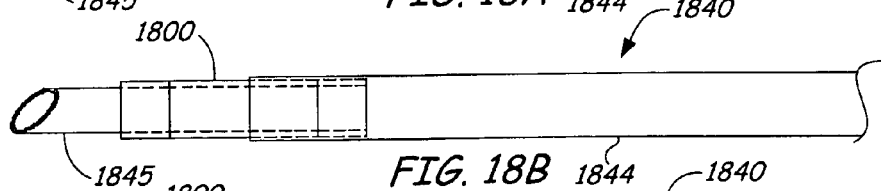
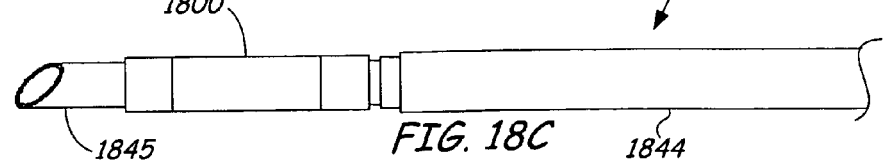

VENTILATION DEVICE AND INSERTION SYSTEM THEREFOR

BACKGROUND

Placement of middle ear ventilation tubes in the tympanic membrane is a common pediatric surgical procedure for the treatment of middle ear infection or otitis media. Also known as tympanostomy tubes or pressure equalizing (PE) tubes, the procedure involves creating an incision (i.e., a myringotomy) in the tympanic membrane and placing a tube in the incision to allow ventilation, pressure equalization and drainage from the middle ear out through the ear canal. The tube can remain in the ear for months or years.

Currently, a tube is placed in the tympanic membrane via visualization through a microscope. A sharp blade is used to create the incision and surgical instruments are used to manipulate the tube into the incision. In the confined space of the ear canal, placement of the tube can be difficult and it is not uncommon for the tube to dislodge from the surgical instrument or for it to accidentally extract from the tympanic membrane before being fully seated, requiring multiple attempts before successful placement is achieved.

Because the middle ear is highly innervated, repeated manipulation of the tympanic membrane is painful enough that patients, especially young children, who make up the majority of tube recipients, require general anesthesia, which is costly and poses additional risks. Surgically inserting the PE tube can be difficult, especially in aligning the flange at one end of the tube with the incision and in the use of multiple different surgical instruments to perform the procedure. In addition, the large retention flanges included in most tubes make them difficult to maneuver in the ear canal and will actually block the clinician's view of the incision site.

The discussion above is merely provided for general background information and is not intended to be used as an aid in determining the scope of the claimed subject matter.

SUMMARY

A ventilation device includes a hollow body having a main portion, at least one distal member coupled to a distal end of the main portion and at least one proximal member coupled to a proximal end of the main portion. The at least one distal member is formed of a shape memory material. The hollow body includes a deployed state for maintaining an opening in an anatomical structure and an undeployed state. The shape memory material forms the at least one distal member into a deployed position. The shape memory material is reversibly deformed from the deployed state into the undeployed state such that at least the distal member changes in shape to an undeployed position, while the main portion of the hollow body remains unchanged.

The main portion includes inner and outer walls extending from the distal end to the proximal end. The outer wall of the main portion is defined by a continuous, fixed outer width. The at least one distal member extends from the distal end of the main portion to an outer end that is located within the defined outer width of the main portion in an undeployed state and the outer end of the at least one distal member is located outwardly from the defined outer width of the main portion in a deployed state. The at least one proximal member extends from the proximal end of the main portion to an outer end that is located outwardly from the defined outer width of the main portion in both an undeployed state and in a deployed state.

An insertion device for inserting the ventilation device is also provided. A hollow sheath member includes a distal end having a cutting edge and a proximal end. The hollow sheath member is configured to at least partially surround the ventilation device. A rod member includes a distal end. The distal end of the rod member is located within the sheath member and is configured to be adjacent the proximal end of the ventilation device. An actuator is configured to hold the distal end of the rod member adjacent to the proximal end of the ventilation device while simultaneously retracting the sheath member from around the ventilation device and sliding it over the rod member.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

FIGS. 7A-7D illustrate yet another embodiment of a ventilation device at least partially comprising a shape memory material.

FIGS. 8A-8B illustrate yet another embodiment of a ventilation device at least partially comprising an elastic deformation material.

FIGS. 9A-9B illustrate a ventilation device at least partially comprising a material that mechanically deforms in-situ when inserted into a tympanic membrane under one embodiment.

FIGS. 10A-10B illustrate ventilation devices that when unconstrained can expand when inserted into a tympanic membrane under one embodiment.

FIGS. 11A-11F illustrate a ventilation device at least partially comprising a shape memory material under yet other embodiments.

FIGS. 12A-12D illustrate different views of an insertion device for use in inserting and deploying the ventilation device of FIGS. 11A-11D under one embodiment.

FIG. 14 illustrates an insertion device for use in inserting and deploying a ventilation device under another embodiment.

FIGS. 16A-16B illustrate an insertion device for use in inserting and deploying a ventilation device under yet another embodiment.

FIG. 17 illustrates an insertion device for use in inserting and deploying a ventilation device under yet another embodiment.

FIGS. 18A-18C illustrate an insertion device for use in inserting and deploying a ventilation device under yet another embodiment.

DETAILED DESCRIPTION

Embodiments described are directed to various ventilation devices and insertion systems for inserting ventilation devices in different membranes of a body. In one particular embodiment, a ventilation device includes a shape memory material that allows the device to remain in a deformed state during insertion into a body. After insertion through the membrane of interest, it is allowed to re-form its flanges or members in-situ to anchor it in place. The deformed ventilation device and the insertion device that places the device in the membrane allows for minimally invasive ventilation system placement, which reduces the pain, cost and risks associated with conventional procedures and devices.

Figure 1:
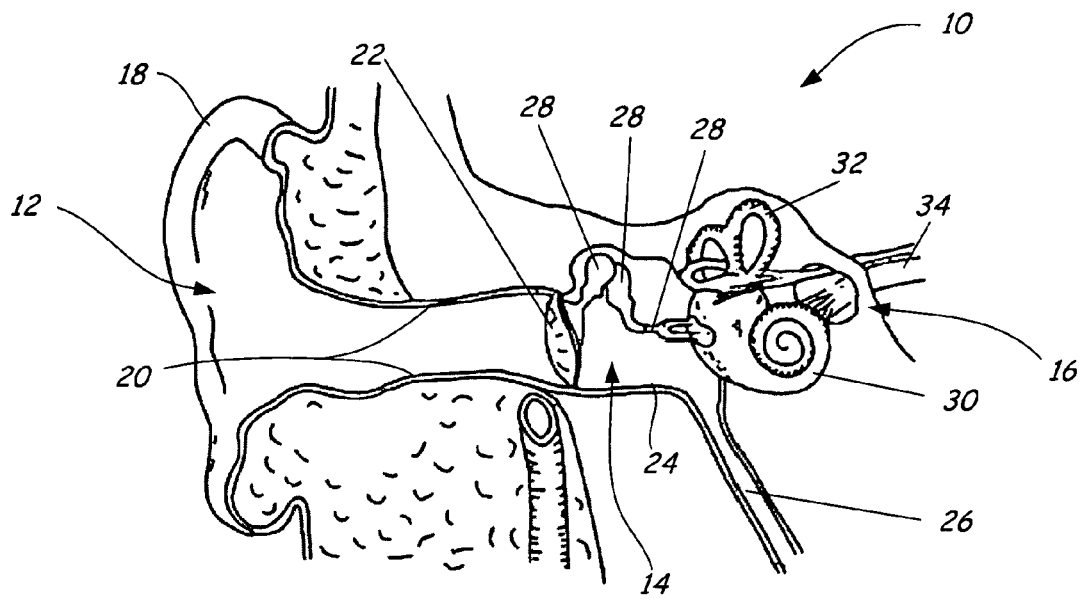
FIG. 1 is a simplified diagrammatic view of an ear.

FIG. 1 illustrates a system of organs in an ear 10 of a body that enables a person to detect sound. Ear 10 is able to change sound pressure waves into a signal of nerve impulses to be processed by the brain. Ear 10 includes an outer ear 12, a middle ear 14 and an inner ear 16. Outer ear 12 collects sound and includes the pinna 18, the ear canal 20 and an outer most layer of the ear drum or tympanic membrane 22. Pinna 18 helps direct sound through ear canal 20 to tympanic membrane 22. Middle ear 14 includes an air-filled cavity 24 having an opening for the Eustachian tube 26 that is located behind tympanic membrane 22. Middle ear 14 also includes ossicles bones 28. Inner ear 16 includes the fluid-filled cochlea 30 and the semicircular canals 32. Cochlea 30 is the auditory portion of the inner ear, while semicircular canals 32 are attuned to both gravity and motion. The ossicles bones 28 transmit sound from the air in cavity 24 to cochlea 30. Fluid in cochlea 30 moves in response to the vibrations coming from middle ear 14. The motion of the fluid is converted to electrical impulses, which travel along the auditory nerve 34 to structures in the brainstem for further processing. Eustachian tube 26 couples cavity 24 of middle ear 14 to the nose and mouth of a human. In a normal state, Eustachian tube 26 is collapsed. However, Eustachian tube 26 can open and close to equalize pressure in cavity 24.

An infection of the middle ear 14 can result in a build up of fluid and increased pressure in cavity 24 causing severe pain. Children are often prone to infections of middle ear 14 because of their underdeveloped Eustachian tube 26. A myringotomy is a surgical procedure in which a tiny incision is created in tympanic membrane 22 to relieve pressure caused by the excessive buildup of fluid due to an infection of the middle ear 14. If a patient requires a myringotomy, this generally suggests that Eustachian tube 26 is either partially or completely obstructed and is not able to perform its proper functions In some cases, besides making an incision in tympanic membrane 22, a ventilation device is inserted into the opening. Insertion of a ventilation or pressure equalizing (PE) device can allow external ventilation of middle ear 14 for an extended period of time. However, in the confined space of ear canal 20, especially an ear canal of a child, insertion of a ventilation device can be difficult. In one example, the incision made in tympanic membrane 22 is often made too large relative to the ventilation device. In such an example, the device will fall out much earlier than desired. In another example, many surgical tools need to be used to insert the device, such as a blade, a funnel (to visualize tympanic membrane 22), forceps (to deliver the device), suction and a microscope. Therefore, much time is needed to prepare for the relatively simple surgery and additional time is needed during the procedure to switch between use of the instruments. Although this relatively brief procedure can be performed on an outpatient basis, in general, children require a general anesthetic such that they remain co-operative during the procedure. Administering anesthetic increases the time of the procedure as well as cost. A device that can alleviate these disadvantages can greatly enhance patient comfort as well as reduce procedural time and undue injury to tympanic membrane 22, while simultaneously simplifying the procedure for physicians.

As discussed above, embodiments described are directed towards devices, systems and procedures for delivering a ventilation structure to a membrane of a body, such as tympanic membrane 22 for treatment of a middle ear infection or otitis media. It should be realized, though, that embodiments described can be used to deliver and maintain an opening in any anatomical structure of the body whether the opening is naturally occurring or surgically created. In addition, embodiments are not limited to just ear ventilation, but could provide communication between any two areas in a body separated by a membrane or barrier. Embodiments described are also directed to the ventilation structure itself.

While embodiments of the ventilation device are illustrated as a hollow body, the device can also be a 'plug' with no internal passageway. A plug could be used to block openings in a membrane, or create a mechanical communication between two spaces separated by a membrane, such as a membrane of a sinus cavity. The device can also be used to create communication between two lumens such as formation of vascular shunts or applied to the gastrointestinal tract and biliary system. The deployed distal members of the device may also provide better positioning of stents, in that, the larger ends can limit movement of the device/stent. For example, tracheal, bronchial, and esophageal stents are at high risk of movement from an originally deployed position. This is likely due to the symmetrical cylinder shape of the stent/device. Also, the device can be a minimally invasive way to deploy a trocar device/site.

The device can also be used in tympanometry. For example, a device that forms an airtight fit around a tympanometry probe could be placed into the ear canal (instead of through the tympanic membrane). The self expanding device would seal off the middle ear, allowing the pressure to be accurately varied in the proximal ear canal. It is also possible that a device delivery system by itself could be used for tympanometry without the need for the device component. Expansion components (such as balloons) on a delivery system could be used to fill and seal off the ear canal.

Figure 2A:
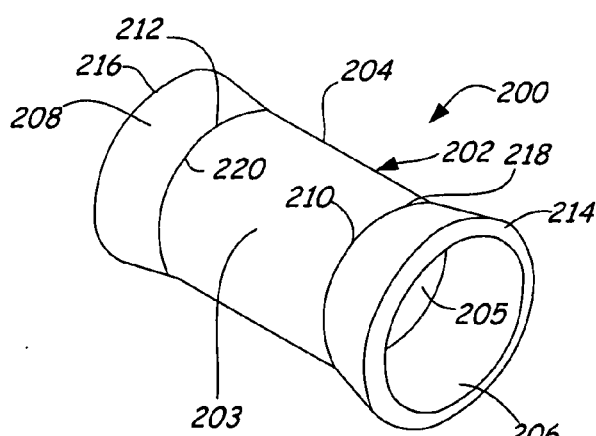
FIGS. 2A-2C illustrate a ventilation device at least partially comprising a shape memory material under one embodiment.
Figure 2B:
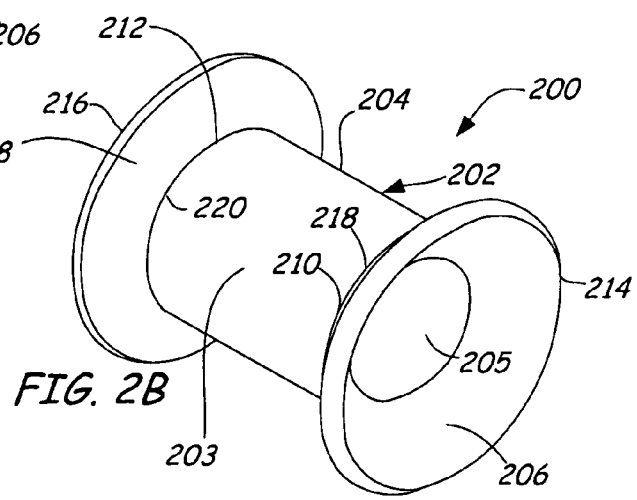
Figure 2C:
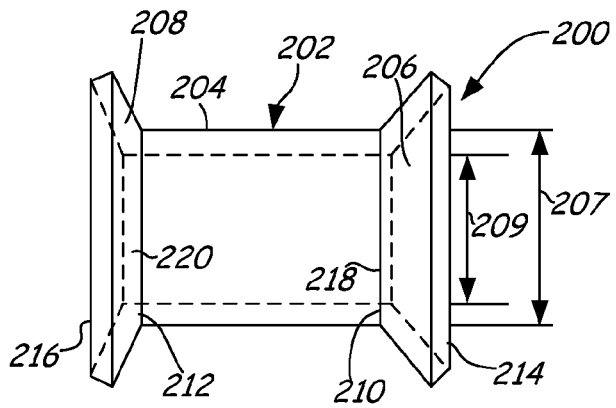

FIGS. 2A-2C illustrate a ventilation device 200 comprised at least partially of a shape memory material in accordance with one embodiment. In the perspective view of FIG. 2A, ventilation device 200 is in an undeployed state. In the perspective view of FIG. 2B and in the side view of FIG. 2C, ventilation device 200 is in a deployed state. Ventilation device 200 includes a hollow body 202 made at least partially of a shape memory metal or polymer. Example shape memory metals include shape memory alloys, such as a nickel-titanium alloy coined Nitinol and various aluminum alloys coined Algiloys (i.e., copper-zinc-aluminum-nickel and copper-aluminum-nickel). Example shape memory polymers include oligo(ε-caprolactone)diol and crystallisable oligo(ρ-dioxanone)diol. However, it should be realized that other types of shape memory alloys and polymers can be used. Although ventilation device 200 is illustrated as having a cylindrical, tube-like structure, other geometries are possible.

In one embodiment, ventilation device 200 is formed at least partially with a shape memory material in the deployed state as illustrated in FIGS. 2B and 2C. After formation, reversible deformation is applied to the ventilation device to place it in the undeployed state as illustrated in FIG. 2A. In the undeployed state, ventilation device 200 is able to be delivered to the tympanic membrane or other anatomical structure for insertion. Upon addition of heat, such as heat applied from a living body, and removal of any mechanical constraint, the ventilation device 200 regains its deployed configuration as illustrated in FIGS. 2B and 2C.

In FIGS. 2A-2C, body 202 of ventilation device 200 includes a main portion 204, a distal member 206 and a proximal member 208. Distal member 206 is coupled to a distal end 210 of main portion 204, while proximal member 208 is coupled to a proximal end 212 of main portion 204. While the entire body 202 can be formed of a shape memory material, it should be realized that it is possible for main portion 204 or parts of main portion 204 to be formed of a different material than the shape memory materials of distal and proximal members 206 and 208.

Main portion 204 includes an outer wall 203 and an inner wall 205. Outer wall 203 and inner wall 205 extend from distal end 210 to proximal end 212. As illustrated in FIG. 2C, outer wall 203 is defined by and includes a continuous, fixed outer width or outer diameter 207 and inner wall 205 is defined by and includes a continuous, fixed inner width or inner diameter 209. In other words, main portion 204 remain unchanged between an undeployed state and a deployed state.

Both distal member 206 and proximal member 208 have outer ends 214 and 216 and inner ends 218 and 220. Inner ends 218 and 220 are coupled to distal end 210 and proximal end 212, respectively, of main portion 204. In the undeployed state or reversible deformation state illustrated in FIG. 2A, outer ends 214 and 216 of members 206 and 208 are located outwardly from the defined outer width 207 of main portion 204. In the deployed state illustrated in FIGS. 2B-2C, distal member 206 and proximal member 208 change their shape such that outer ends 214 and 216 of members 206 and 208 are located outwardly even further from the defined outer width 207 of main portion 204 than that of the location of outer ends 214 and 216 of members 206 and 208 in the undeployed state.

As more clearly illustrated in FIG. 2C, although outer ends 214 and 216 of members 206 and 208 are located outwardly from the defined width 207 of main portion 204 by the same distance, it is possible that distal member 206 has a greater distance between outer end 214 and inner end 218 than a distance between outer end 216 and inner end 220 of proximal member 208. In such an embodiment, a taper between outer end 214 and inner end 218 of distal member 206 is much more gradual compared to a taper between outer end 216 and inner end 220 of proximal member 208. Inserting distal member 206 that has a gradual taper compared to proximal member 208 having a more rapid taper into tympanic membrane 22 (FIG. 1) will ensure that the device will not fall into cavity 24 (FIG. 1), while still allowing it to eventually fall out through ear canal 20 (FIG. 1).

Figure 3:
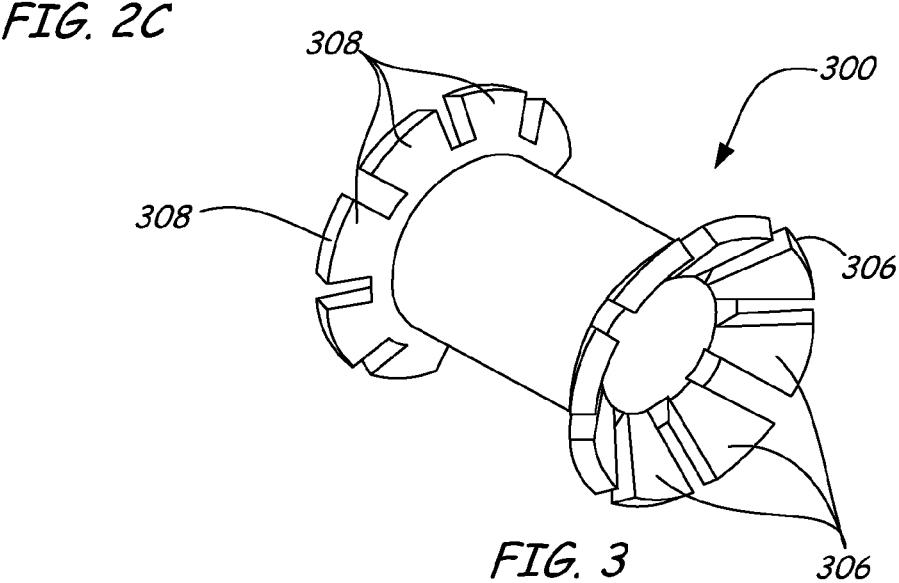
FIG. 3 illustrates a ventilation device at least partially comprising a shape memory material under another embodiment.

FIG. 3 illustrates a perspective view of a ventilation device 300 comprised at least partially of shape memory material in accordance with another embodiment. Ventilation device 300 is also formed with a shape memory alloy or polymer similar to ventilation device 200, except, device 200 includes a plurality of distal members 306 and proximal members 308. While there is no difference in the intended functionality of device 300 compared to device 200, the reduction in material of having a plurality of members 306 and 308 instead of a single member allows device 300 to regain the flanged or grommet shape more quickly while maintaining a low profile during insertion into the tympanic membrane. Additionally, the plurality of members 306 and 308, can allow deformations that could not be achieved with a single member or solid flange.

Figure 4A:
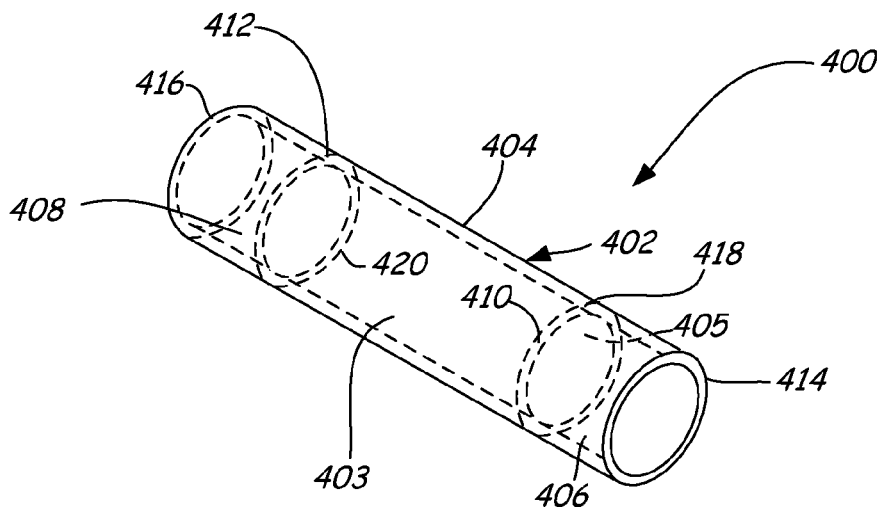
FIGS. 4A-4C illustrate a ventilation device at least partially comprising a shape memory material under yet another embodiment.
Figure 4B:
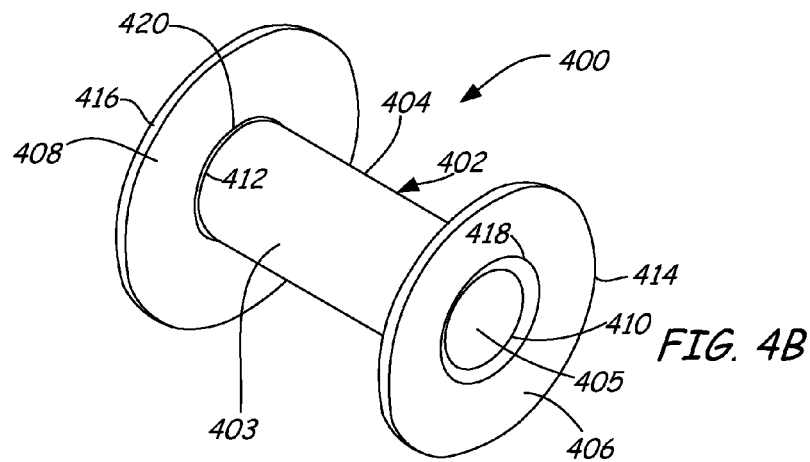
Figure 4C:
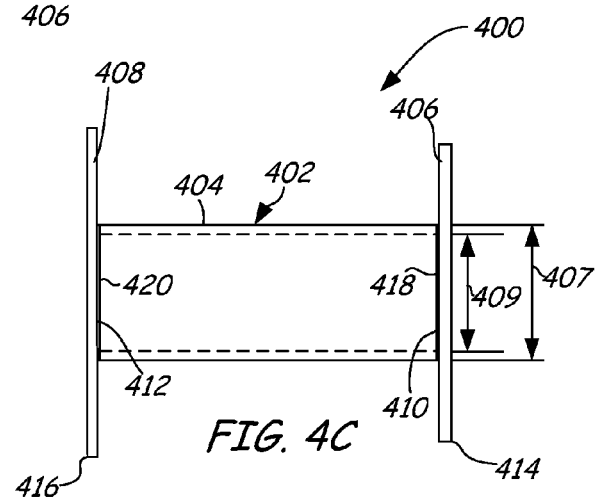

FIGS. 4A-4C illustrate a ventilation device 400 comprised at least partially of a shape memory material in accordance with yet another embodiment. In the perspective view of FIG. 4A, ventilation device 400 is in an undeployed state. In the perspective view of FIG. 4B and in the side view of FIG. 4C, ventilation device 400 is in a deployed state. Like ventilation devices 200 and 300, ventilation device 400 includes a hollow body 402 made at least partially of a shape memory metal or shape memory polymer. Although ventilation device 400 is illustrated as having a cylindrical, tube-like structure, other geometries are possible.

In one embodiment, ventilation device 400 is formed at least partially with a shape memory material in the deployed state as illustrated in FIGS. 4B and 4C. After formation, reversible deformation is applied to ventilation device 400 to place it in the undeployed state as illustrated in FIG. 4A. In the undeployed state, ventilation device 400 is able to be delivered to a membrane or other anatomical structure for insertion. Upon addition of heat, such as heat applied from body temperature and removal of any mechanical constraint, ventilation device 400 regains its deployed configuration as illustrated in FIGS. 4B and 4C.

In FIGS. 4A-4C, body 402 of ventilation device 400 includes a main portion 404, a distal member 406 and a proximal member 408. Distal member 406 is coupled to a distal end 410 of main portion 404, while proximal member 408 is coupled to proximal end 412 of main portion 404. While the entire body 402 can be formed of a shape memory material, it should be realized that it is possible for main portion 404 or parts of main portion 404 to be formed of a different material than the shape memory materials of distal and proximal members 406 and 408.

Main portion 404 includes an outer wall 403 and an inner wall 405. Outer wall 403 and inner wall 405 extend from distal end 410 to proximal end 412. As illustrated in FIG. 4C, outer wall 403 is defined by and includes a continuous, fixed outer width or outer diameter 207 and inner wall 405 is defined by and includes a continuous, fixed inner width or inner diameter 209. In other words, main portion 404 remain unchanged between an undeployed state and a deployed state.

Both distal member 406 and proximal member 408 have outer ends 414 and 416 and inner ends 418 and 420. Inner ends 418 and 420 are coupled to distal end 410 and proximal end 412, respectively, of main portion 404. In the undeployed state or reversible deformation state illustrated in FIG. 4A, outer ends 414 and 416 of members 406 and 408 extend from distal end 210 and proximal end 212 and are located within the defined outer width 407 of main portion 404. In the deployed state illustrated in FIGS. 4B and 4C, distal member 406 and proximal member 408 change their shape such that outer ends 414 and 416 of members 406 and 408 are located outwardly from the defined outer width 407 of main portion 404. As more clearly illustrated in FIG. 4C, it is possible that a distance from outer end 414 to inner end 418 of distal member 406 is smaller than a distance from outer end 416 to inner end 420 of proximal member 408. Inserting distal member 406 into tympanic membrane 22 will ensure that the device will not fall into cavity 24 (FIG. 1), while still allowing it to eventually fall out through ear canal 20 (FIG. 1).

Figure 5A:
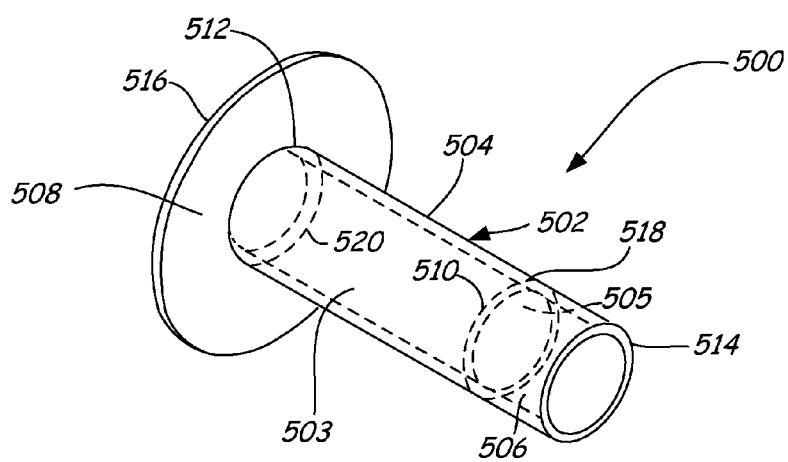
FIGS. 5A-5C illustrate a ventilation device at least partially comprising a shape memory material under yet another embodiment.
Figure 5B:
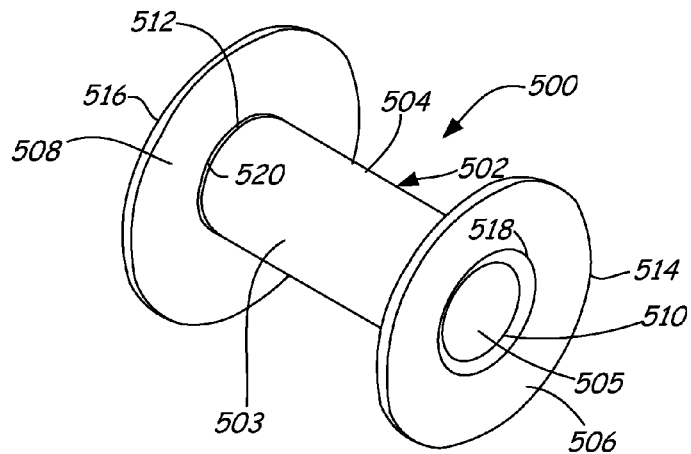
Figure 5C:
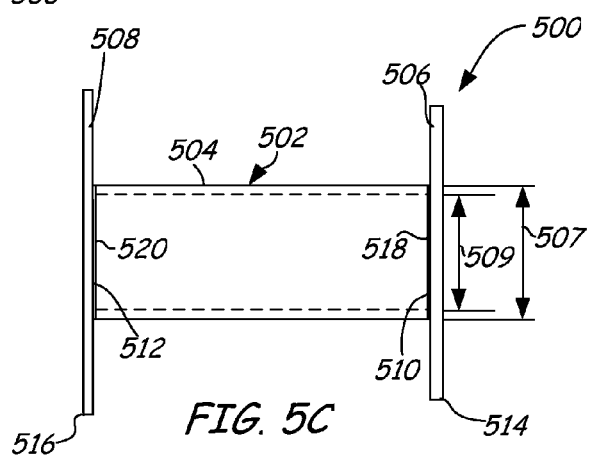

FIGS. 5A-5C illustrate a ventilation device 500 at least partially comprised of a shape memory material in accordance with yet another embodiment. In the perspective view of FIG. 5A, ventilation device 500 is in an undeployed state. In the perspective view of FIG. 5B and in the side view of FIG. 5C, ventilation device 500 is in a deployed state. Like ventilation devices 200, 300 and 400 ventilation device 500 includes a hollow body 502 made of a shape memory metal or polymer. Although ventilation device 500 is illustrated as having a cylindrical, tube-like structure, other geometries are possible.

In one embodiment, ventilation device 500 is formed with a shape memory material in the deployed state as illustrated in FIGS. 5B and 5C. After formation, reversible deformation is applied to ventilation device 500 to place it in the undeployed state as illustrated in FIG. 5A. In the undeployed state, ventilation device 500 is able to be delivered to tympanic membrane 22 or other anatomical structure for insertion. Upon addition of heat, such as heat applied from body temperature and removal of any mechanical constraint, ventilation device 500 regains its deployed configuration as illustrated in FIGS. 5B and 5C.

In FIGS. 5A-5C, body 502 of ventilation device 500 includes a main portion 504, a distal member 506 and a proximal member 508. Distal member 506 is coupled to a distal end 510 of main portion 504, while proximal member 508 is coupled to proximal end 512 of main portion 504. While the entire body 502 can be formed of a shape memory material, it should be realized that it is possible for main portion 504 or parts of main portion 504 to be formed of a different material than the shape memory material of distal member 406.

Main portion 504 includes an outer wall 503 and an inner wall 505. Outer wall 503 and inner wall 505 extend from distal end 510 to proximal end 512. As illustrated in FIG. 5C, outer wall 503 is defined by and includes a continuous, fixed outer width or outer diameter 507 and inner wall 505 is defined by and includes a continuous, fixed inner width or inner diameter 509. In other words, main portion 504 remain unchanged between an undeployed state and a deployed state.

Both distal member 506 and proximal member 508 have outer ends 514 and 516 and inner ends 518 and 520. Inner ends 518 and 520 are coupled to distal end 510 and proximal end 512, respectively, of main portion 504. In the undeployed state or reversible deformation state illustrated in FIG. 5A, outer end 514 of distal member 506 extends from distal end 510 and located within the defined outer width 507 of main portion 504, while proximal member 508 extends from proximal end 512 and is located outwardly from the defined outer width 507 of main portion 504. In other words, in the undeployed state, proximal member 508 is pre-formed or pre-deployed and is unaffected by heat. In one embodiment, proximal member 508 can be made of a material other than a shape memory material. However, proximal member 508 can also be made of a shape memory material that has already been pre-deployed through a heating process such that it is pre-formed. In the deployed state illustrated in FIGS. 5B and 5C, distal member 506 changes its shape such that outer end 514 of member 506 is located outwardly from the defined outer width 507 of main portion 504, while proximal member 508 does not change its shape. As more clearly illustrated in FIG. 5C, it is possible that a distance from outer end 514 to inner end 518 of distal member 506 is smaller than a distance from outer end 516 to inner end 520 of proximal member 508. Inserting distal member 506 into tympanic membrane 22 (FIG. 1) will ensure that the device will not fall into the cavity 24 (FIG. 1), while still allowing it to eventually fall out through ear canal 20 (FIG. 1).

FIGS. 6A-6D illustrate a ventilation device 600 at least partially comprising an elastically deformable material in accordance with one embodiment. Example materials that demonstrate elastic deformation upon application of a constraint and are able to return to an undeformed state upon removal of the constraint include a number of biocompatible metals such as Titanium, Silver, Tantalum, alloys of stainless steel, Cobalt Chromium, Alumina, Titanium etc; as well as polymers such as polyolefins, polyurethanes, Silicone, PEEK, PMMA, fluoropolymers and others known to those familiar in the art. In the perspective view of FIG. 6A and the side view of FIG. 6B, ventilation device 600 is in a deployed state. In the perspective view of FIG. 6C and in the side view of FIG. 6D, ventilation device 600 is in an undeployed state. Like ventilation devices 200, 300, 400 and 500 ventilation device 600 includes a hollow body 602. At least a portion of body 602 is made of a material that can be elastically deformed into a position for delivery to a membrane or other anatomical structure for insertion. Upon release of the elastic deformation, body 602 returns to its non-deformed state and again forms its deployed configuration. Although ventilation device 600 is illustrated as having a cylindrical, tube-like structure, other geometries are possible.

In FIGS. 6A-6D, body 602 of ventilation device 600 includes a main portion 604, a plurality of distal members 606 and a plurality of proximal members 608. While the entire body 602 can be formed of an elastically deformable material, it should be realized that it is possible for main portion 604 to be formed of a different material than the elastic deformation materials of distal and proximal members 606 and 608. Distal members 606 are coupled to a distal end 610 of main portion 604, while proximal members 608 are coupled to proximal end 612 of main portion 604. Distal members 606 and proximal members 608 have outer ends 614 and 616 and inner ends 618 and 620. Inner ends 618 and 620 are coupled to distal end 610 and proximal end 612, respectively, of main portion 604.

Figure 6A:
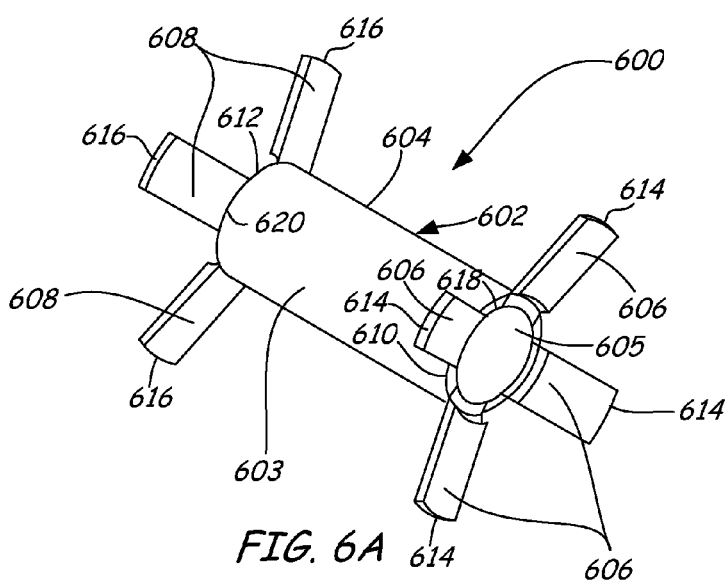
FIGS. 6A-6D illustrate a ventilation device at least partially comprising an elastic deformation material under one embodiment.
Figure 6B:
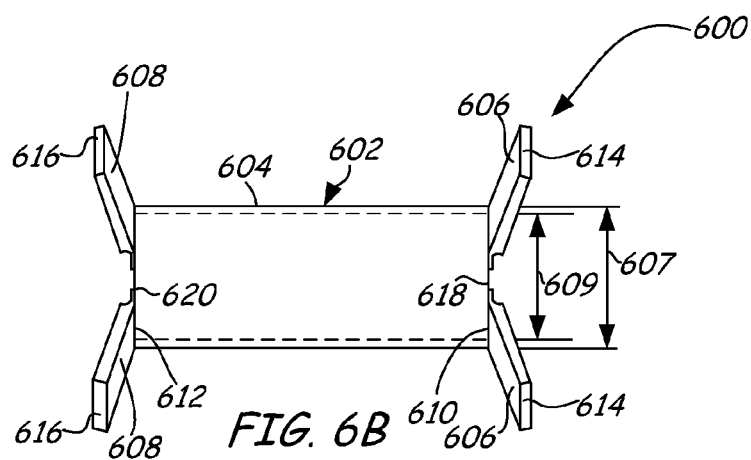

Main portion 604 includes an outer wall 603 and an inner wall 605. Outer wall 603 and inner wall 605 extend from distal end 610 to proximal end 612. As illustrated in FIG. 6B, outer wall 603 is defined by and includes a continuous, fixed outer width or outer diameter 607 and inner wall 605 is defined by and includes a continuous, fixed inner width or inner diameter 609. In other words, main portion 604 remains unchanged between an undeployed state and a deployed state.

Figure 6C:
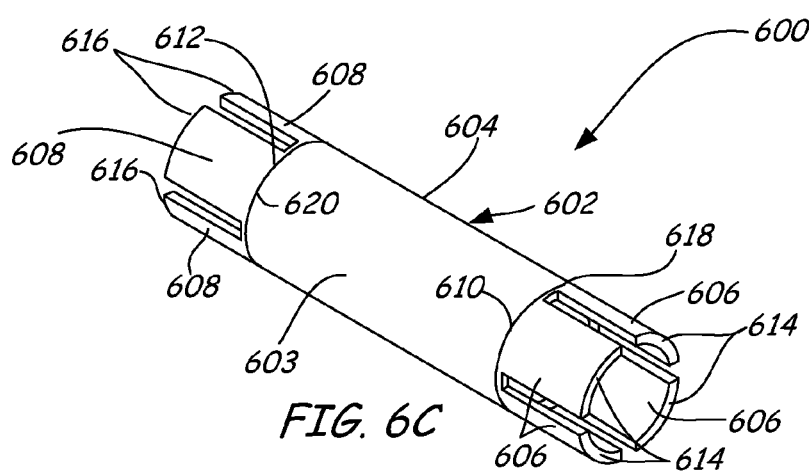
Figure 6D:
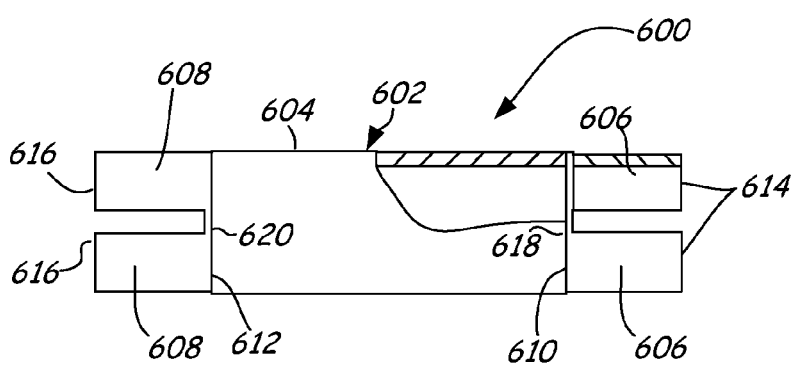

In the undeployed state illustrated in FIGS. 6C and 6D where ventilation device is constrained into an elastically deformed position, outer ends 614 and 616 of distal members 606 and proximal members 608 extend from distal end 610 and proximal end 612 and are located within the defined outer width 607 of main portion 604. In the deployed state illustrated in FIGS. 6A and 6B where the constraining component is removed, distal members 606 and proximal members 608 return to their non-deformed state such that outer ends 614 and 616 of members 606 and 608 are located outwardly from the defined outer width 607 of main portion. Although not particularly illustrated in FIGS. 6A-6D, it is possible that that a distance from outer ends 614 to inner ends 618 of distal members 606 are smaller than a distance from outer ends 616 to inner ends 620 of proximal members 608 to ensure that the device will not fall into cavity 24 (FIG. 1), while still allowing it to eventually fall out through ear canal 20 (FIG. 1) from tympanic membrane 22 (FIG. 1).

FIGS. 7A-7D illustrate another embodiment of a ventilation device 700 comprised at least partially of shape memory material. In the perspective view of FIG. 7A and the side view of FIG. 7B, ventilation device 700 is in an undeployed state and has a constraining component 722. In the perspective view of FIG. 7C and in the side view of FIG. 7D, ventilation device 700 is in a deployed state with hollow body 702 moved axially relative to constraining component 722 for formation of ventilation device 700. Like ventilation devices 200, 300, 400, 500 and 600, ventilation device 700 includes a hollow body 702 located under constraint component 722. In the embodiment illustrated in FIGS. 7A-7D, body 702 (shown in dashed lines in FIG. 7A) can be at least partially made of a shape memory material, such as a shape memory alloy or polymer, which is reversibly deformable under constraining component 722. Although ventilation device 700 is illustrated as having a cylindrical, tube-like structure, other geometries are possible. Upon releasing constraining component 722 and upon addition of heat, body 702 can be returned to its undeformed state and again form its deployed configuration illustrated in FIGS. 7C and 7D.

In general, the constraint mechanisms shown and described are all external to the body in its deformed/undeployed state. It some cases it is possible to provide internal mechanisms to constrain the device from returning to its undeformed state. For example, in the case of the elastically deformed example, an internal sheath could be provided that would fit into undercuts formed into the internal flange on the device, holding the internal flange in the deformed state for deployment through a membrane. Retracting the internal crimping sheath from the undercuts would then allow the body to return to its undeformed state to form an internal flange. This type of design could be advantageous in cases where a pre-formed external flange would prevent the use of an external crimping sheath.

In FIGS. 7A-7D, body 702 of ventilation device 700 includes a main portion 704, a distal member 706 and a proximal member 708. Distal member 706 is coupled to a distal end 710 of main portion 704, while proximal member 708 is coupled to a proximal end 712 of main portion 704. While the entire body 702 can be formed of a shape memory material, it should be realized that it is possible for main portion 704 or parts of main portion 704 to be formed of a different material than the shape memory material of distal member 706.

Main portion 704 includes an outer wall 703 and an inner wall 705. Outer wall 703 and inner wall 705 extend from distal end 710 to proximal end 712. As illustrated in FIG. 5C, outer wall 703 is defined by and includes a continuous, fixed outer width or outer diameter 707 an inner wall 705 is defined by and includes a continuous, fixed inner width or inner diameter 709. In other words, main portion 704 remains unchanged between an undeployed state and a deployed state.

Both distal member 706 and proximal member 708 have outer ends 714 and 716 and inner ends 718 and 720. Inner ends 718 and 720 are coupled to distal end 710 and proximal end 712, respectively, of main portion 704. In an undeployed state or reversible deformation state illustrated in FIG. 7A, outer end 714 of distal member 706 extends from distal end 710 and is located within the defined outer width 707 of main portion 704, while proximal member 708 extends from proximal end 712 and is located outwardly from the defined outer width 707 of main portion 704. In other words, in the undeployed state, proximal member 708 is pre-formed or pre-deployed. It will be unaffected by heat. In one embodiment, proximal member 708 can be made of a material other than a shape memory material. However, proximal member 708 can also be made of a shape memory material that has already been pre-deployed through a heating process such that it is pre-formed. In the deployed state illustrated in FIGS. 7C and 7D where body 702 moves axially relative to constraining component 722, distal member 706 is exposed to heat to return to a non-deformed shape such that outer end 714 of member 706 is located outwardly from the defined outer width 707 of main portion 704, while proximal member 708 does not change its shape.

Figure 7A:
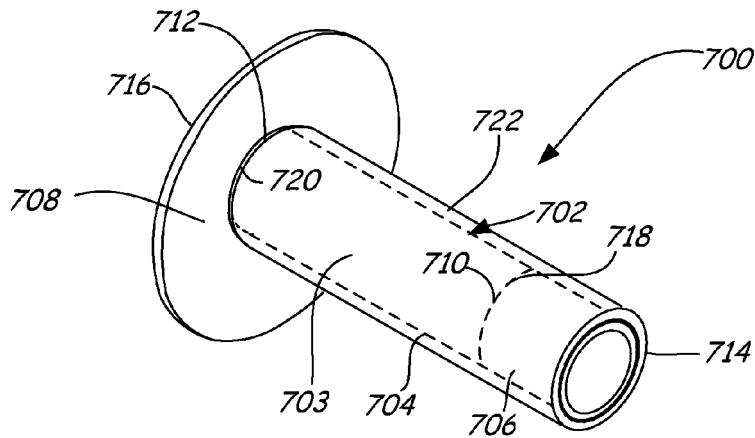
Figure 7B:
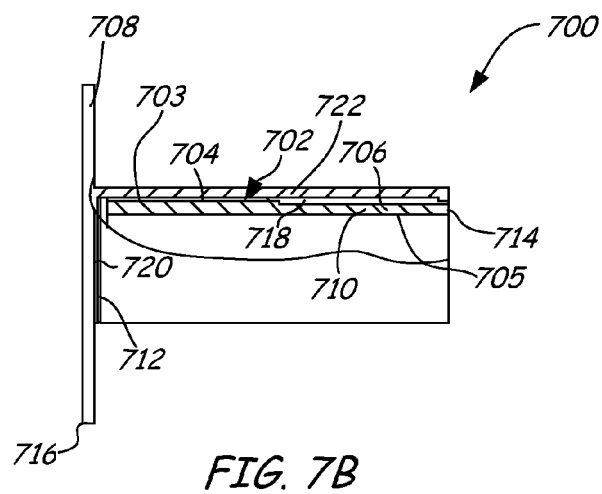
Figure 7C:
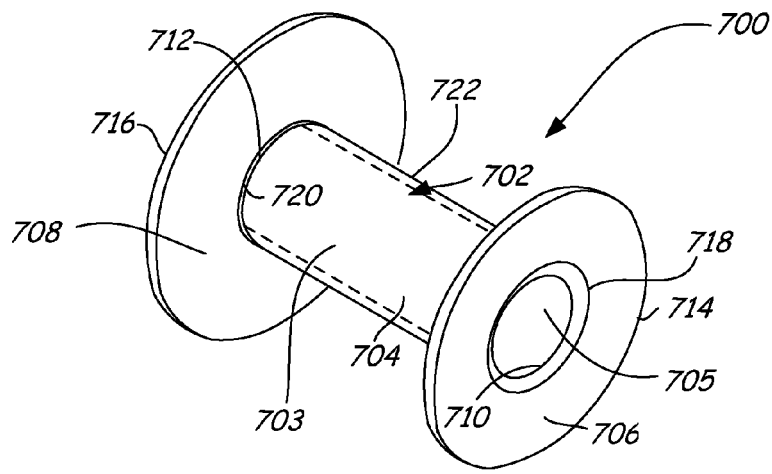

As illustrated in FIGS. 7C and 7D, it is possible that a distance from outer end 714 to inner end 618 of distal member 706 is smaller than a distance from outer end 716 to inner end 720 of proximal member 708 when ventilation device 700 is in a deployed state to ensure that the device will not fall into cavity 24 (FIG. 1), while still allowing it to eventually fall out through ear canal 20 (FIG. 1) from tympanic membrane 22 (FIG. 1).

FIGS. 8A-8B illustrate yet another embodiment of a ventilation device 800 comprising an elastically deformable material. In the perspective view of FIG. 8A, ventilation device 800 is in an undeployed state and has a constraining component 822. In the perspective view of FIG. 8B, ventilation device 800 is in a deployed state with a hollow body 802 moved relative to constraining component 822 for formation of ventilation device 800. Like ventilation devices 200, 300, 400, 500, 600 and 700, ventilation device 800 includes hollow body 802 located under constraining component 822. In the embodiment illustrated in FIGS. 8A-8B, body 802 (shown in dashed lines in FIG. 8A) can be made of an elastically deformable material, which is deformed under constraining component 822. Upon sliding body 802 relative to constraining component 822, a portion of body 802 can be returned to its non-deformed state and again form its deployed configuration illustrated in FIG. 8B. Although ventilation device 800 is illustrated as having a cylindrical, tube-like structure, other geometries are possible.

In FIGS. 8A-8B, body 802 of ventilation device 800 includes a main portion 804, a plurality of distal members 806 and a proximal member 808. Distal members 806 are coupled to a distal end 810 of main portion 804, while proximal member 808 is coupled to proximal end 812 of main portion 804. While the entire body 802 can be formed of an elastically deformed material, it should be realized that it is possible for main portion 804 or parts of main portion 804 to be formed of a different material than the elastically deformable material of distal member 806.

Main portion 804 includes an outer wall 803 and an inner wall 805. Outer wall 803 and inner wall 805 extend from distal end 810 to proximal end 812. As illustrated in FIG. 8B, outer wall 803 is define by and includes a continuous, fixer outer width or outer diameter 807 and inner wall 805 is defined by and includes a continuous, fixed inner width or inner diameter 809. In other words, main portion 804 remains unchanged between an undeployed state and a deployed state.

Distal members 806 and proximal member 808 have outer ends 814 and 816 and inner ends 818 and 820. Inner ends 818 and 820 are coupled to distal end 810 and proximal end 812, respectively, of main portion 804. In the undeployed state illustrated in FIG. 8A where ventilation device 800 is constrained into an elastically deformed position, outer ends 814 of distal members 806 extend from distal end 810 are located within the defined outer width 807 of main portion 804, while outer end 816 of proximal member 808 extends from proximal end 812 and is located outwardly from the defined outer width 807 of main portion 804. In other words, in the undeployed state, proximal member 808 is a pre-formed or pre-deployed. In the deployed state illustrated in FIGS. 8A and 8B where the device 802 is slid axially relative to constraining component 822, distal members 806 return to their non-deformed state such that outer ends 814 of members 806 are located outwardly from the defined outer width 807 of main portion 804, while proximal member 808 does not change its shape.

As illustrated in FIGS. 8A-8B, it is possible that a distance from outer end 814 to inner end 818 of distal members 806 is smaller than a distance from outer end 816 to inner end 820 of proximal member 808 when ventilation device 800 is in a deployed state to ensure that the device will not fall into cavity 24 (FIG. 1), while still allowing it to eventually fall out through ear canal 20 (FIG. 1) from tympanic membrane 22 (FIG. 1).

FIGS. 9A-9B illustrate a ventilation device 900 comprised of a material that can be mechanically deformed in-situ in accordance with one embodiment. In the perspective view of FIG. 9A, ventilation device 900 is in an undeployed state. In the perspective view of FIG. 9B, ventilation device 900 is in a deployed state. Like ventilation devices 200, 300, 400, 500, 600, 700, and 800, ventilation device 900 includes a hollow body 902 made of a mechanically deformable material, which can be one of a number of biocompatible materials such as Titanium, Silver, Tantalum, alloys of stainless steel, Cobalt Chromium, Alumina, Titanium etc; as well as polymers such as polyolefins, polyurethanes, Silicone, PEEK, PMMA, fluoropolymers and others known to those familiar in the art. In one embodiment, ventilation device 900 is formed with a material in the undeployed state as illustrated in FIG. 9A. After formation, device 900 is delivered to tympanic membrane 22 (FIG. 1) for insertion. To place ventilation device 900 in the deployed state as illustrated in FIG. 9B, body 902 is deformed in-situ. Although ventilation device 900 is illustrated as having a cylindrical, tube-like structure, other geometries are possible.

In FIGS. 9A-9B, body 902 of ventilation device 900 includes a main portion 904, a distal end 910 and a proximal end 912. Body 902 includes a first set of slots 924 formed about a periphery of body 902 adjacent to distal end 910 and a second set of slots 926 formed about a periphery of body 902 adjacent to proximal end 912. Slots 924 and 926 are formed through a thickness of body 902 between each of ends 910 and 912, but do not intersect ends 910 and 912. Between each slot 924 and 926 includes material of body 902. In the undeployed state, material between each slot 924 and 926 remains in alignment with body 902. In a deployed state as illustrated in FIG. 9B, material between each slot 924 and 926 is deformed to form a distal member 906 and a proximal member 908. Slots 924 and 926 provide portions of body 902 that can more easily deform. In FIG. 9B, a part of each slot is folded to face against a remaining part of each slot. Distal member 906 and proximal member 908 have widths that are greater than the width of main portion 904. Device 900 is inserted into tympanic membrane 22 as illustrated in FIG. 9A and mechanically deformed into a shape as illustrated in FIG. 9B while device 900 is in-situ. The shape of FIG. 9B will ensure that the device will not fall into cavity 24 (FIG. 1) and can eventually fall out through ear canal 20 (FIG. 1). It should be obvious to those skilled in the art that a number of different geometric shapes can be used to achieve the same results as slots shown in FIG. 9A.

It should be noted that FIG. 9B could be an 'elastic deformation' embodiment as well as a 'deformed in-situ' embodiment. A part could be formed into the shape of FIG. 9B out of an appropriately elastic material. It could subsequently be constrained to a deformed shape similar to that of FIG. 9A. Release of the constraining force would result in the device elastically returning to its original shape (FIG. 9B).

FIGS. 10A-10B illustrate other embodiments of ventilation devices 1000A and 1000B comprising an elastically deformable material. In the perspective view of FIG. 10A, ventilation device 1000A is in deployed or undeployed state and in the perspective view of FIG. 10B, ventilation device 1000B is in deployed states. Ventilation device 1000A include a bodies 1002A having a first axial edge 1028A and second axial edge 1030A. Body 1002A is made of elastic deformable material such that it can be rolled from first axial edge 1028A to second axial edge 1030A to form a hollow tubular shape.

In an undeployed state, the rolled hollow shape of body 1002A is compressed (or more tightly rolled) such that its diameter is smaller than the diameter in its deployed state. In its deployed state, body 1002A expands (or unrolls). The rolling and unrolling of body 1002A provides device 1000A the requisite deformation for maintaining an opening in a membrane in a body without the need for proximal or distal members. In the undeployed state, ventilation device 1000A is able to be delivered to a membrane in a body for insertion. Upon removal of a mechanical constraint, ventilation device 1000A regains its deployed configuration.

In the perspective view, FIG. 10B illustrates ventilation device 1000B in a deployed state having a pair of distal members 1006 attached to a distal end 1010. Like the rolled embodiment illustrated in FIG. 10A, distal members 1006 are compressed (more tightly rolled) such they are located close to each other. In the deployed state illustrated in FIG. 10B, members 1006 expand or unrolls. The rolling or unrolling body 1002A provides device 1000B the requisite deformation for maintaining an opening in a membrane in a body. In the undeployed state, ventilation device 1000B is able to be delivered to a membrane in a body for insertion. Upon removal of a mechanical constraint, ventilation device 1000B regains its deployed configuration.

FIGS. 11A-11D illustrate a ventilation device 1100 comprised at least partially of a shape memory material, such as a shape memory metal or polymer, in accordance with yet another embodiment. It should be realized however, ventilation device 1100 can be made of other types of materials or combinations of other types of materials and shape memory materials. In the perspective view of FIG. 11A, ventilation device 1100 is in a first undeployed state. In the perspective view of FIG. 11B and in the side view of FIG. 11C, ventilation device 1100 is in a deployed state. In the perspective view of FIG. 11D, ventilation device 1100 is in a second undeployed state. Like other above-described ventilation devices, ventilation device 1100 includes a hollow body 1102. Although ventilation device 1100 is illustrated as having a cylindrical, tube-like structure, other geometries are possible.

Figure 11C:
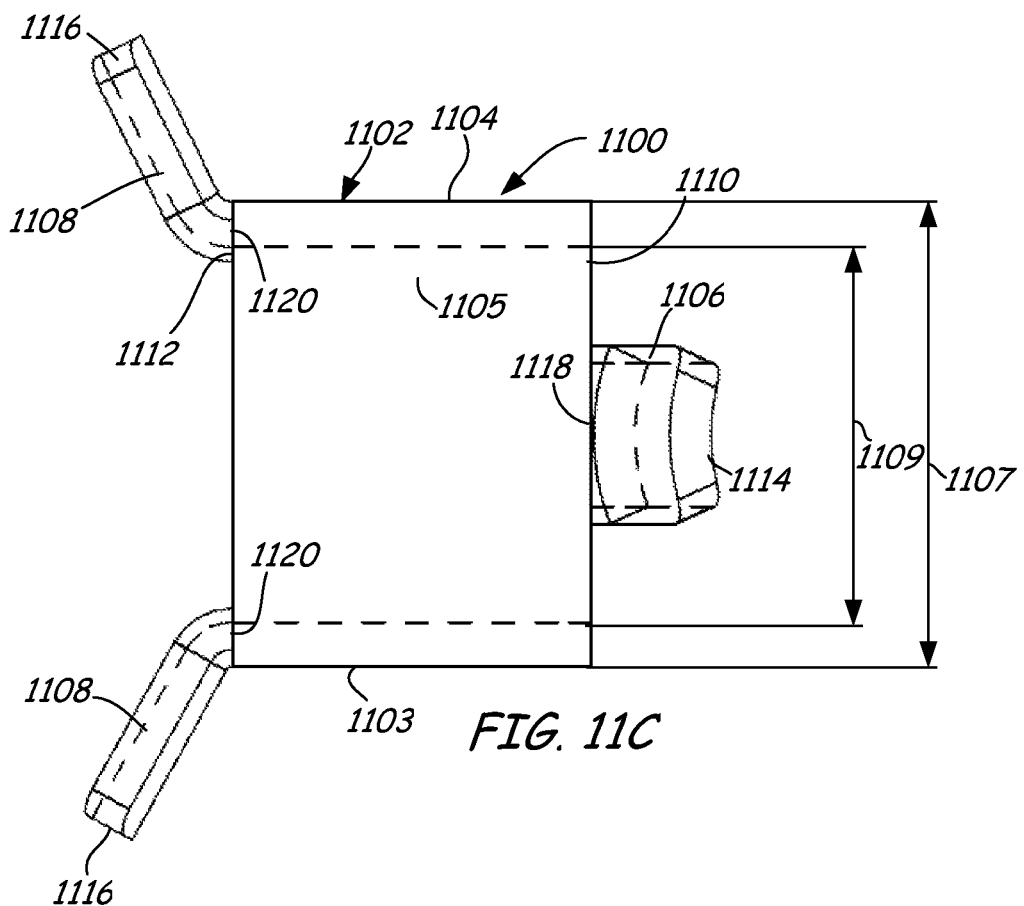
Figure 11D:
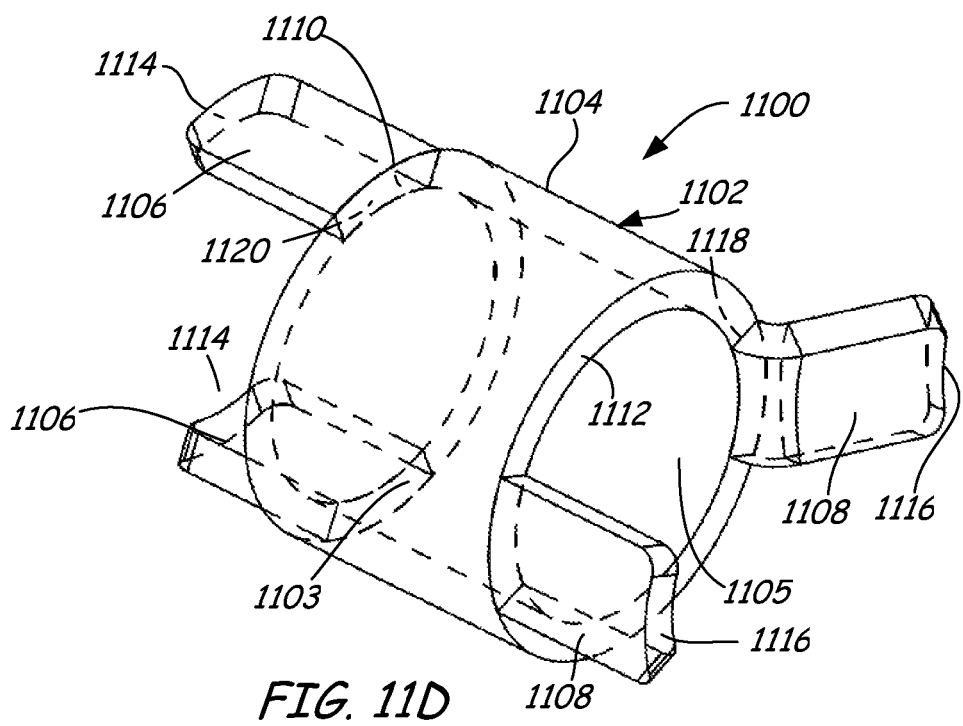

In one embodiment, at least a portion of ventilation device 1100 is formed with a shape memory material in the deployed state as illustrated in FIGS. 11B and 11C. After formation, reversible deformation is applied to ventilation device 1100 to place it in the first undeployed state as illustrated in FIG. 11A or in the second undeployed state as illustrated in FIG. 11D. In either the first or second undeployed states, ventilation device 1100 is able to be delivered to a membrane in a body for maintaining an opening in the membrane. Upon addition of heat, such as heat applied from body temperature and removal of any mechanical constraint, ventilation device 1100 regains its deployed configuration as illustrated in FIGS. 11B and 11C.

In FIGS. 11A-11D, hollow body 1102 of ventilation device 1100 includes a main portion 1104, a pair of distal members 1106 and a pair of proximal members 1108. However, it should be realized that other quantities are possible. Distal members 1106 are coupled to a distal end 1110 of main portion 1104, while proximal members 1108 are coupled to proximal end 1112 of main portion 1104. While the entire body 1102 can be formed of a shape memory material, it should be realized that it is possible for main portion 1104 or parts of main portion 1104 to be formed a different material than the shape memory material Main portion 1104 includes an outer wall 1103 and an inner wall 1105. Outer wall 1103 and inner wall 1105 extend from distal end 1110 to proximal end 1112. As illustrated in FIG. 11C, outer wall 1103 is defined by an includes a continuous, fixed outer width or outer diameter 1107 and inner wall 1105 is defined by and includes a continuous, fixed inner width or inner diameter 1109. In other words, main portion 1104 remains unchanged between an undeployed state and a deployed state.

The thickness between outer wall 1103 and inner wall 1105 of main portion 1104 and the wall thickness of distal and proximal members 1106 and 1108 can be the same or different. A thin wall between outer wall 1103 and inner wall 1105 of main portion 1104 is desirable because it maximizes the internal diameter (in the case of a tube-like geometry), while minimizing the external diameter (in the case of a tube-like geometry). A large internal diameter is beneficial because it provides a greater cross-sectional area for venting and prevents plugging. The thickness between outer wall 1103 and inner wall 1105 should be great enough to provide the structural properties necessary to prevent the device from being crushed or squeezed closed. However, the thickness between outer wall 1103 and inner wall 1105 should be thin enough to allow the necessary deformation between the deployed and undeployed states to remain in the elastic or super-elastic ranges and to prevent cracking or failure at the deformation points. For example, wall thicknesses of the proximal and distal members 1106 and 1108 as well as the thickness between outer wall 1103 and inner wall 1105 of main portion 1104 can be approximately between 0.0015 to 0.020 inches. In tympanic membrane applications, wall thicknesses of approximately between 0.0015 to 0.008 inches are sufficient to prevent crushing while still minimizing the outer diameter of the vent and insertion device and providing ease of placement and visualization in confined spaces. In sinus applications, wall thicknesses of approximately greater than 0.005 inches are necessary to prevent crushing. It should be noted, the wall thicknesses described require that a rigid or semi-rigid material, such as Nitinol, be used. Wall thicknesses for vents made of silicone rubber, for example, would need to be thicker to maintain an open vent, while rigid plastic may require thicker walls for strength.

Distal members 1106 and proximal members 1108 have outer ends 1114 and 1116 and inner ends 1118 and 1120. Inner ends 1118 and 1120 are coupled to distal end 1110 and proximal end 1112, respectively, of main portion 1104. In the first undeployed state or first reversible deformation state illustrated in FIG. 11A, outer ends 1114 and 1116 of distal members 1106 and proximal members 1108 extend from distal end 1110 proximal end 1112 and are located within the defined outer width 1107 of main portion. In the deployed state illustrated in FIGS. 11B and 11C, distal members 1106 and proximal members 1108 return to their non-deformed state such that their outer ends 1114 and 1116 extend from distal end 1110 and proximal end 1112 and are located outwardly from the defined outer width 1107 of main portion 1104.

In one embodiment, members 1106 and 1108 can be made of a shape memory material, while main portion 1104 can be made of other types of materials. As illustrated in FIGS. 11A-11D, members 1106 extend from distal end 1110 of main portion 1104. Each member 1106 is coupled to and positioned about main portion 1104 180 degrees from each other. In other words, each member 1106 is positioned opposite from each other and facing each other on distal end 1110. Members 1108 extend from proximal end 1112 of main portion 1104. Each member 1108 is coupled to and positioned about main portion 1104 180 degrees from each other. In other words, each member 1108 is positioned opposite from each other and facing each other on proximal end 1112. It should be realized that members 1106 and 1108 can be located at different positions from each other than illustrated. For example, a first distal member can be located about distal end 1110 between 0 and 180 degrees from the second distal member. Likewise, a first proximal member can be located about proximal end 1112 between 0 and 180 degrees from the second proximal member.

Each member 1108 is located about proximal end 1112 similar to each member 1106 located about distal end 1110. However, each member 1108 is located about proximal end 1112 approximately 90 degrees from the location of each member 1106 around distal end 1110. These orientations of members 1106 and 1106 are clearly illustrated in the side view of FIG. 11C. It should be realized, though, that the embodiments illustrated in FIGS. 11A-11D are exemplary and various other configurations are possible. For example, each member 1108 can be located about proximal end 1112 between 0 and 90 degrees from the location of each member 1106.

In the first undeployed state or first reversible deformation state illustrated in FIG. 11A, the outer ends 1116 of members 1106 and 1108 extend from distal end 1110 and proximal end 1112 and are located within the outer width 1107 of main portion 1104. In the second undeployed state or second reversible deformation state illustrated in FIG. 11D, the outer ends 1114 of distal members 1106 extend from distal end 1110 and are located within in the outer width 1107 of main portion 1104. However, the outer end 1116 of one of the proximal members 1108 extends from proximal end 1112 and is located within the outer width 1107 of main portion 1104, but the outer end 1116 of the other of the proximal members 1108 extends from proximal end 1112 and is located outwardly from the defined outer width 1107 of main portion 1104. In other words, in the second undeployed state, one of members 1108 is pre-formed or pre-deployed and is unaffected by heat. In one embodiment, the pre-deployed member 1108 can be made of a material other than a shape memory material. However, both members 1108 can also be made of a shape memory material that has already been pre-deployed through a heating process such that it is pre-formed. In the deployed state illustrated in FIGS. 11B and 11C, Both members 1106 and one of members 1108 changes their shape while the other of member 1108 that was pre-deployed does not change its shape.

A ventilation device can be coated with various materials to provide added benefit. For example, antimicrobial coatings could be applied to limit formation of biofilm, prevent premature blocking, limit infection, etc. Silver coating can also be applied to any of the materials used to make the ventilation device by pulsed deposition in a plasma vacuum chamber.

Biofilm formation on the ventilation device may be delayed by the use of a biologic coating such as elastin, or collagen, laminin, etc. In another example, the device could be drug eluting. Drugs eluted from the surface of the device can provide anesthetic effects, limit the growth of cells on or near the device, promote the growth of cells on or near the device, or provide a local drug treatment. In fact, a ventilation device could itself deliver cells to focal regions. Ventilation devices can be treated to allow visualization with various medical imaging systems, such as radio opaque markers. In addition, a ventilation device can be made of biodegradable material (such as polymeric materials including co-polymers of PLA & PGA, Tyrosine polycarbonate, or metal alloys such as Iron and Magnesium).

FIGS. 11E and 11F illustrate additional alternative embodiments of ventilation device 1100 in deployed positions. It would be possible, using the same shape memory materials described in the aforementioned embodiments, to have at least one distal member or flange 1106, at least one proximal member or flange 1108, or both, that deform or extend inwardly when deployed, while the other of the members deform or extend outwardly when deployed or remain same between the undeployed and deployed states. In other words, at least one of the outer end 1114 of distal member 1106 and/or at least one of the outer end 1116 of proximal member 1108 are located inwardly from the defined width of main portion 1104 when deployed. Flanges and/or members that deform inwardly could be combined in any fashion with other distal or proximal members or flanges included in device 1100 that are located outwardly from the defined width of main portion 1104. One could have the outer end of at least one member located inwardly from the defined width of main portion 1104 on one, both or neither end in a deployed state, along with the outer end of at least one member located outwardly from the defined width of main portion 1104 on one, both, or neither end in a deployed state. It would also be possible, with the inward deployment state, to create a plug instead of a vent, for example, to close or seal off a pre-existing hole in an anatomical structure.

For example, in FIG. 11E, ventilation device 1100 includes outer ends 1114 of distal members 1106 as being located inwardly from the defined width of main portion 1104 in a deployed state, while outer ends 1116 of proximal members 1108 are located outwardly from the defined width of main portion 1104 in the deployed state. The inwardly deployed ends 1114 could create a plug. As noted earlier, but not illustrated, outer ends 1114 of distal members 1106 could be located outwardly from the defined width of main portion 1104 in a deployed state, while outer ends 1116 of proximal member 1108 could be located inwardly from the defined width of main portion 1104 in the deployed state.

For example, in FIG. 11F, ventilation device 1100 includes an outer end 1114 of at least one of the distal members 1106 as being located inwardly from the defined width of main portion 1104 in a deployed state and an outer end 1114 of the other of the distal members as being located outwardly from the defined width of main portion 1104 in the deployed state, while the outer end 1116 of at least one or more of the proximal members 1108 is located outwardly from the defined width of main portion 1104 in the deployed state. As noted earlier, but not illustrated, an outer end 1116 of at least one of the proximal members 1108 could be located inwardly from the defined width of main portion 1104 in a deployed state and an outer end 1114 of the other of the proximal members as being located outwardly from the defined width of main portion 1104 in the deployed state, while the outer end 1114 of at least one or more of the distal members 1106 is located outwardly from the defined width of main portion 1104 in the deployed state. It should be realized that any variation of each distal or proximal member on device 1100 could be located outwardly from the defined width of main portion 1104, located inwardly from the defined width of main portion 1104 or in alignment with the define width of main portion 1104 in a deployed state.

Figure 12A:
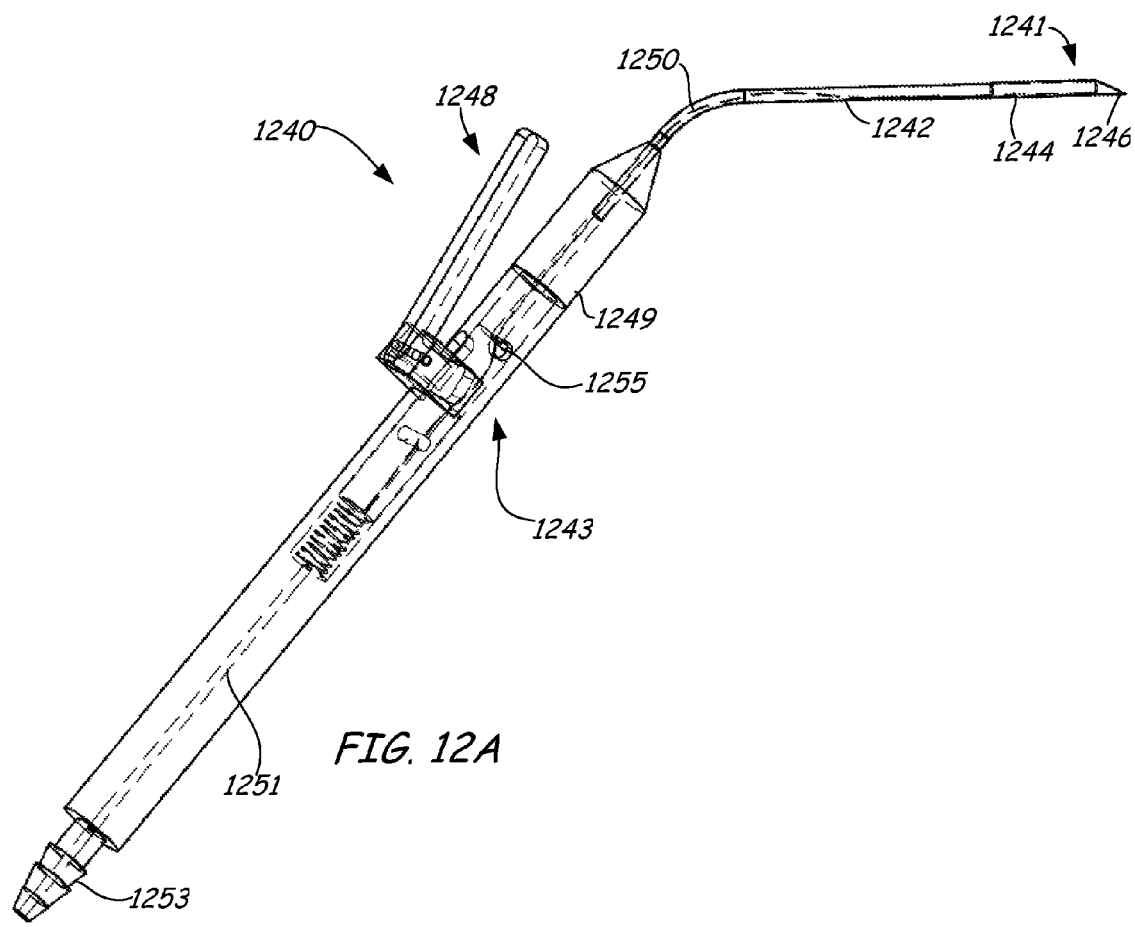

FIG. 12A illustrates a perspective view of an insertion system 1240 in accordance with one embodiment. Insertion system 1240 is configured for use in inserting ventilation device 1100 (FIGS. 11A-11D) into an anatomical structure of a body. Insertion system 1240 includes an insertion end or distal end 1241 including a rod member 1242 and a sheath member 1244, which has a cutting edge 1246. Sheath member 1244 surrounds a portion of rod member 1242 at insertion end 1241.

Insertion system 1240 includes an actuation end 1243 including an actuator 1248, a handle 1249 and a flexible actuation member 1250 coupling the actuator to the sheath member 1244. Flexible actuation member 1250 is made of a flexible material, such as plastic or thin metal wire. Rod member 1242 protrudes from handle 1249 and bends along an angle. For example, rod member 1242 can be bent from handle 1249 at an angle of approximately 60 degrees. However, it should be realized that other angles are possible. Flexible actuation member 1250 runs from a portion of actuator 1248 housed within handle 1249 until it reaches an aperture in rod member 1242 where flexible actuation member 1250 moves to the outside of the device and is coupled to sheath member 1244.

Insertion system 1240 also includes a suction member 1251 located within handle 1249 and coupled to a fitting 1253 for attachment to a suction line. Handle also includes apertures 1255. When inserting insertion end into an anatomical cavity and after cutting edge 1246 forms an incision in an anatomical structure of a body, the clinician may need to remove fluid. To remove the fluid, the clinician can cover apertures 1255 to direct the suction force provided by suction member 1251 to the insertion end 1249. Thereby, fluid can be drained away from the anatomical structure through the sheath member 1244 and the rod member 1242 and outwards through the suction member 1251.

In general, a ventilation device, such as ventilation device 1100 is loaded onto insertion system 1240 at the insertion end 1241. With sheath member 1244 surrounding the distal end of rod member 1244, the distal ends of rod member 1244 and sheath member 1244 are inserted into an ear canal or other anatomical cavity. The cutting edge 1246 of sheath member 1244 makes an incision in an anatomical structure, such as a tympanic membrane. After the membrane is cut and the sheath member 1244 is located far enough through the membrane, actuator 1248 is actuated to pull sheath member 1244 back, while rod member 1242 allows ventilation device 1100 to remain in place. The delivery and insertion of device 1100 will be described in detail below.

FIG. 12A illustrates one type of actuator 1248. Other variations of actuators are possible as long as the actuator is able to keep a distal end of rod member 1242 rigidly against a ventilation device to hold the ventilation device in place during sheath member 1244 insertion and sheath member removal. For example, actuator 1248 includes a spring, an arm and flexible actuation member 1250 coupled to the spring, the arm and the sheath member 1244. To remove sheath member 1244 without moving rod member 1242 or the ventilation device, the arm can be actuated to pull on the flexible actuation member 1250.

FIG. 12B illustrates an enlarged perspective view of the sheath member 1244 illustrated in FIG. 12A. Sheath member 1244 is a hollow member made of a metallic material having a distal end 1252 and a proximal end 1253. Distal end 1252 includes cutting edge 1246 that forms part of a tapered distal end 1252. Distal end 1252 tapers from one side of the hollow member to the other side of the hollow member such that the length of sheath member 1244 is shorter on one side than the other side. The side with the longer length terminates at cutting edge 1246. Although not specifically illustrated in FIGS. 12A-12D, distal end 1252 of sheath member can include other topographies than that which is illustrated. For example, the tapered proximal end can also include certain bevels or beveled edges to make cutting edge 1246 more conducive for piercing a membrane to mitigate resistive forces from the membrane. Sheath member 1244 also includes a slot 1254. Slot 1254 includes a distal end 1256 and a proximal end 1257. Distal end 1256 of slot 1254 is in communication with tapered end or distal end 1252 of sheath member 1244.

FIG. 12C illustrates an enlarged perspective view of the insertion end 1241 of insertion system 1240 and FIG. 12D illustrates a side sectional view of insertion end 1241 of insertion system 1240. FIGS. 12C and 12D illustrate a portion of rod member 1242, the sheath member 1244, a portion of flexible actuation member 1250 and the ventilation device 1100 loaded onto the device. Rod member 1242 includes an aperture 1258 where flexible actuation member 1250 moves from a position within system 1240 and within rod member 1242 to a position external to system 1240 or rod member 1242 such that it can couple to sheath member 1244 at a coupling point 1260. Flexible actuation member 1250 can couple to sheath member 1244 by solder, for example. However, other forms of attachment are possible.

A distal end 1262 of rod member 1242 and its external surface are positioned within and adjacent an internal surface of sheath member 1244. In other words, sheath member 1244 surrounds the distal end 1262 of rod member 1242. Ventilation device 1100 is loaded within sheath member 1244 such that the sheath member encloses device 1100 except where slot 1254 is located in the sheath member. Ventilation device 1100 is also loaded such that distal end 1262 of rod member 1242 is adjacent proximal end 1112 of device 1100.

As illustrated in FIGS. 12C and 12D, ventilation device 1100 is in the second undeployed state or second reversible deformation state illustrated in FIG. 11D when loaded onto insertion system 1240. More specifically, the outer ends 1114 of distal members 1106 extend from distal end 1110 within the defined outer width 1107 (FIG. 11C) of main portion 1104 (FIGS. 11A-11D). However, the outer end 1116 of one of the proximal members 1108 extends from proximal end 1112 within the defined outer width 1107 of main portion 1104, but the outer end 1116 of the other of the proximal members 1108 extends from proximal end 1112 outwardly from the defined outer width 1107 of main portion 1104. This member 1108 extends from away from rod member 1242 and through slot 1254 of sheath member 1244. Such a pre-deployed member 1108 acts as a visual indicator to a clinician. As will be discussed more thoroughly in FIGS. 13A-13D, the clinician will insert sheath member 1244 through an anatomical structure only as far as the location of the pre-deployed member 1108.

Figure 13A:
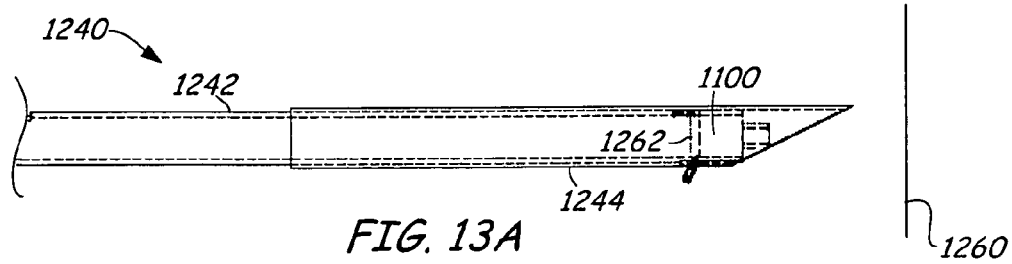
FIGS. 13A-13D illustrate a process of inserting and deploying the ventilation device of FIGS. 11A-11D using the insertion device illustrated in FIGS. 12A-12C under one embodiment.
Figure 13B:
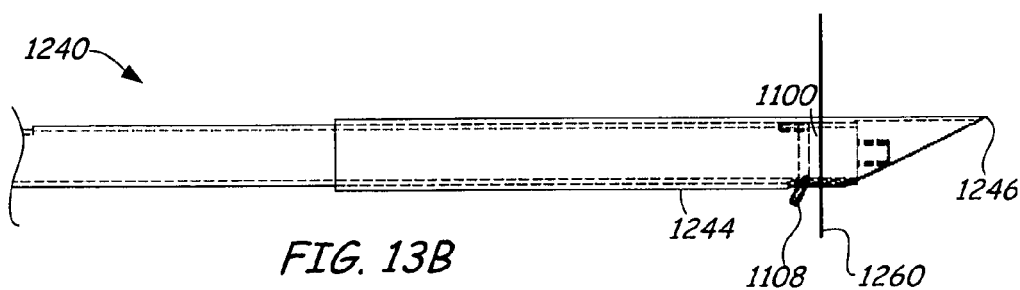
Figure 13C:
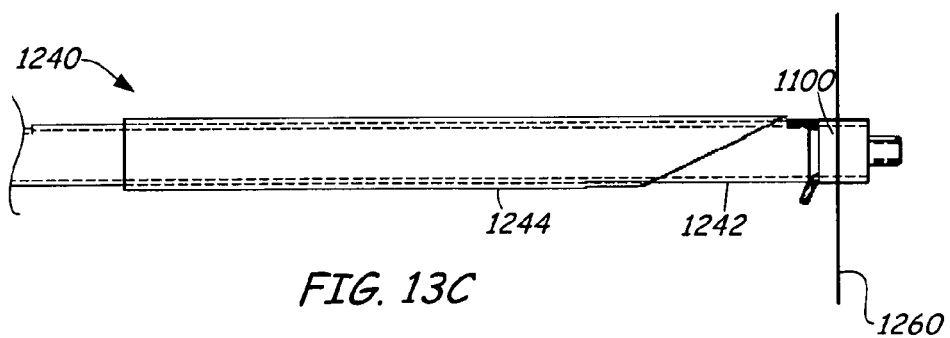
Figure 13D:
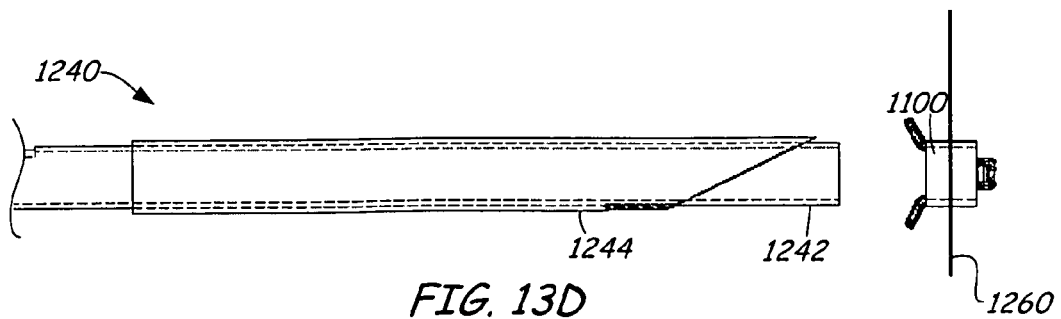

FIGS. 13A-13D illustrate a process of inserting and deploying the ventilation device 1100 of FIGS. 11A-11D into an anatomical structure 1260 using the insertion system 1240 illustrated in FIGS. 12A-12D under one embodiment. In FIGS. 13A-13C, ventilation device 1100 is shown in the second undeployed state or second reversible deformation state illustrated in FIG. 11D. In FIG. 13D, ventilation device 1100 is shown in the deployed state illustrated in FIGS. 11B and 11C.

In FIG. 13A, insertion system 1240 has been inserted into an anatomical cavity of a body in preparation for insertion into anatomical structure 1260. As illustrated, sheath member 1244 surrounds distal end 1262 of rod member 1242 and ventilation device 1100. In FIG. 13B, cutting edge 1246 of sheath member 1244 slices through anatomical structure 1260 such that a distal end of the sheath member is inserted through structure 1260 until a clinician can visually see the pre-deployed member 1108 of ventilation device 1100 is next to structure 1260.

In FIG. 13C, the clinician actuates insertion system 1240 such that sheath member 1244 is pulled out of anatomical structure 1260 along the length of rod member 1242, while the rod member remains fixed in place to make sure ventilation device 1100 remains inserted in anatomical structure 1260. Upon ventilation device 1100 being heated by the body, the ventilation device deploys into a deployed state as illustrated in FIG. 13D. Then, the clinician pulls insertion system 1240 including sheath member 1244 and rod member 1242 back through the anatomical cavity and away from the ventilation device 1100 now positioned and deployed in anatomical structure 1260.

FIG. 14 illustrates a side view of an insertion end of an insertion device 1440 in accordance with another embodiment. Insertion system 1440 is configured for use with the ventilation devices 200, 300, 400 and 600 illustrated in FIGS. 2, 3, 4 and 6. In FIG. 14, insertion system 1440 includes a cutting member 1445, a rod member 1442 and a sheath member 1444. Cutting member 1445 includes a cutting edge 1446 for use in piercing a membrane, such as a tympanic membrane. However, cutting member 1445 can also be used to both aspirate fluids out of the ear and/or to deliver local analgesics, antibiotics, etc. Cutting member 1445, rod member 1442 and sheath member 1444 are all cylindrically shaped bodies that are nested within each other. In particular, rod member 1442 surrounds cutting member 1445 and sheath member 1444 surrounds both rod member 1442 and cutting member 1445. A ventilation device 1400 is mounted around cutting member 1445. Sheath member 1444 holds device 1400 in a deformed state, as applicable for an elastically deformable device (i.e., device 500) or hold device 1400 in a reversibly deformed state, as applicable for a shape memory material device, such as devices 100, 200 and 300. Rod member 1442 holds device 1400 in position as sheath member 1444 is retracted. Sheath member 1444 is retracted once device 1400 is successfully positioned. In FIG. 14, ventilation device 1400 is shown with sheath member 1444 partly retracted. However, device 1400 normally would be completely inside sheath member 1444 until it is in position for deployment.

As also illustrated, sheath member 1444 includes positioning marker bands 1401 and 1403. Positioning marker bands 1401 and 1403 are for use in allowing a clinician to visualize when device 1400 is correctly inserted into a membrane or other anatomical structure. In particular, one marker band 1401 is placed on one side of a membrane or anatomical structure and the other marker band 1402 is placed on the other side of the membrane to show correct placement.

Marker bands 1401 and 1403 are an example of a visual indicator to aid the user in determining when the insertion device is correctly placed for deployment. A clear or translucent sheath member can also serve this same function to allow the user to see the device and to position it correctly. A combination of marker bands and a clear crimping sheath can also be employed. Marker bands can be on the device, but visible through the crimping sheath. It is necessary to ensure that the insertion device does not block visual access to the application/deployment site. For example, when a ventilation device is to be placed through a membrane in a constrained space, such as in ear-tube applications, an appropriate 'bend' in the delivery system (for example, a 30, 45, 60, or 90 degree bend) that allows the user to actuate the device deployment mechanism without blocking their site lines could be incorporated with any of the embodiments discussed. A flexible delivery system could also be employed. An example 60 degree bend is illustrated in FIG. 12A in insertion system 1240. Such a system would allow the user to flex the delivery system in any direction favorable to maintaining sight lines.

Figure 15:
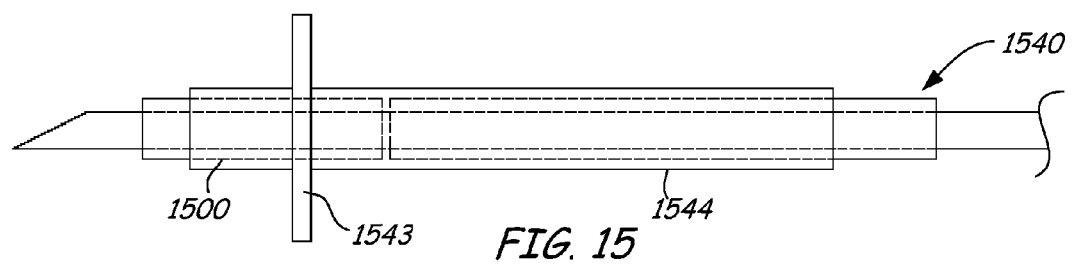
FIG. 15 illustrates an insertion device for use in inserting and deploying a ventilation device under yet another embodiment.

FIG. 15 illustrates a side view of an insertion end of an insertion system 1540 in accordance with another embodiment. Insertion device 1540 is similar to system 1440 except instead of including positioning marking bands, sheath member 1544 includes a stop 1543 to allow a clinician to place the device correctly. Stop 1543 will prevent a clinician from inserting system 1540 any further into a middle ear such that device 1500 will have a correct placement for deployment.

Physical stops, as illustrated in FIG. 15 can be included on the crimping sheath as one example of a mechanical positioning aid. However, stops can also be present that are not located on the sheath member. For example, a completely redundant component could incorporate a stop, so that the stop remains stationary while the sheath member is retracted to ensure the correct placement is maintained during deployment. In the embodiment illustrated in FIGS. 12A-12D, a pre-deployed portion of the ventilation device can be used as a positioning aid by placing it flush against (or at some offset from) the outside of the membrane.

FIG. 16A illustrates a side view of a portion of a cutting member 1645 and FIG. 16B illustrates a side view of a portion of an insertion system 1640 including cutting member 1645 in accordance with an embodiment in which ventilation device 1600 is deformed in-situ. As illustrated in FIGS. 16A and 16B, cutting member 1645 has a device (i.e., bumper or stop) 1680 that allows a distal end 1610 of ventilation device 1600 to be deformed to a flange like structure. In another embodiment, device 1680 can be either expanded or retracted similar to a balloon to allow deformation of the ends of the tubular structure into a flange or grommet like structure. Device 1680 can be present either at both ends or just at distal end 1610 so that once a member or members are deployed or created in-situ, the device will not fall into a cavity (such as the middle ear), while still allowing it to eventually fall out through the ear canal from the tympanic membrane.

FIG. 17 illustrates a side view of another embodiment of an insertion system 1740 which can be used to create an in-situ ventilation device or grommet 1700. A cutting member 1745 includes a device 1780, such as a stop or bumper that is used to deform the ventilation device 1700. Device 1780 is expandable and retractable by applying relative motion via a sheath member 1744.

Figure 19A:
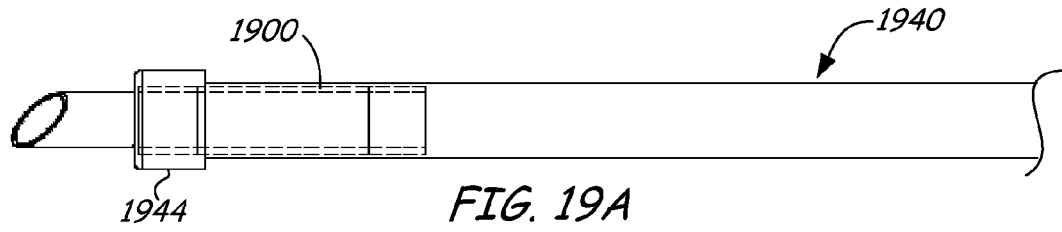
FIGS. 19A-19C illustrate an insertion device for use in inserting and deploying a ventilation device under yet another embodiment.
Figure 19B:
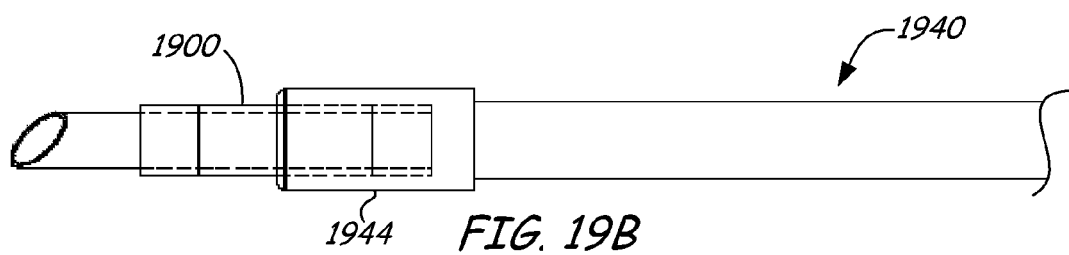
Figure 19C:
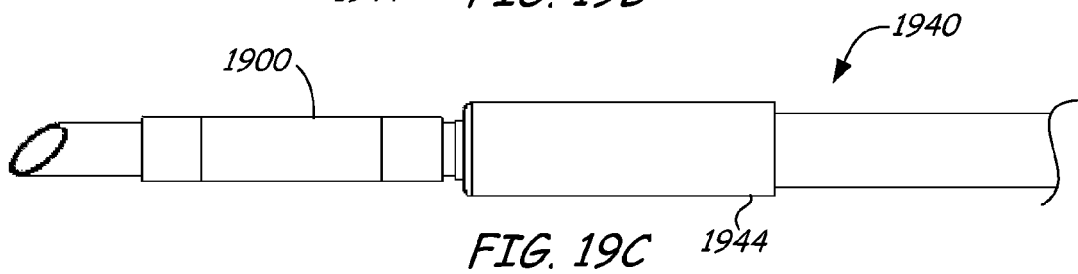

FIGS. 18A-18C and FIGS. 19A-19C illustrates embodiments of insertion systems 1840 and 1940 for inserting shape memory ventilation devices. In FIGS. 18A-18C, a sheath member 1844 is used to constrain a ventilation device 1800. When the sheath member 1844 is pulled back, it allows the end or ends of the ventilation device 1800 to deploy into a flange shape. Sheath member 1844 and cutting member 1845 are then pulled out of the auditory canal leaving the ventilation device 1800 in the tympanic membrane. In FIGS. 19A-19C, a sheath member 1944 is used to keep the undeployed ventilation device 1900 constrained into a low profile shape. The difference with the version illustrated in FIGS. 18A-18C is that the sheath member 1944 deploys by rolling back on itself. The version illustrated in FIGS. 18A-18C allows a lower profile while the latter one may allows a smoother delivery and deployment of the ventilation device 1900.

Figure 20:
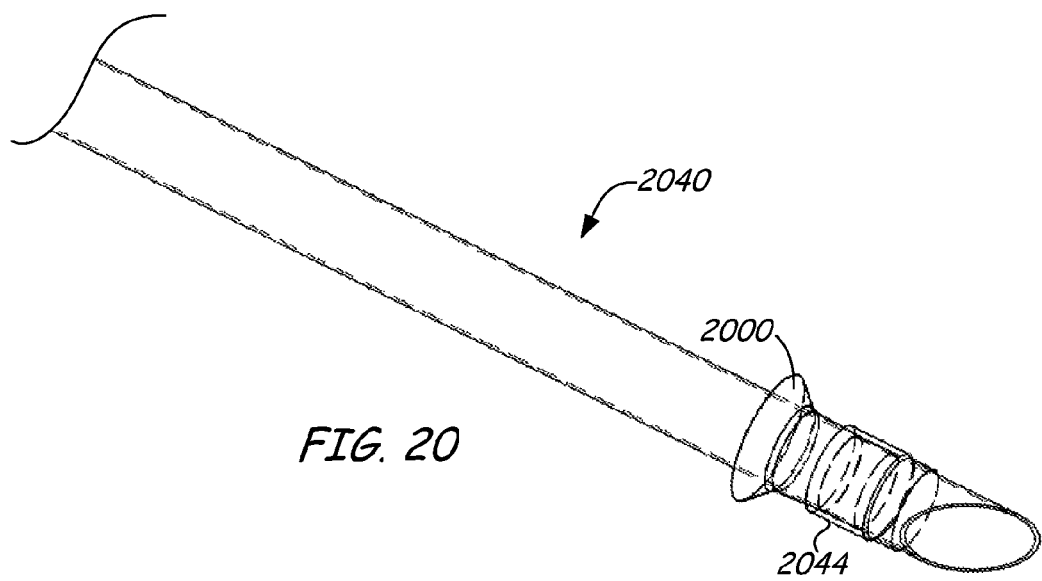
FIG. 20 illustrates an insertion device for use in inserting and deploying a ventilation device under yet another embodiment.

FIG. 20 illustrates a perspective view of an insertion system 2040 having a sheath member 2044 located proximal to the device 2000. This arrangement allows for the proximal member of the device 2000 to be preformed or pre-deployed, acting as a positioning aid and ensuring that the device cannot be deployed too deeply. Sheath member 2044 is located distal to device 2000 and is used to constrain the distal member. FIG. 20 illustrates the device ready for deployment.

All the embodiments of the insertion systems described above may require a lubricious coating on the ventilation device and/or the sheath member to allow the device to be inserted or deployed efficiently. In one embodiment, any of the ventilation devices mentioned above may be spray-coated or dip-coated in a mixture of latex or a polymer such as silicone and an antimicrobial agent such as nitrofurazone. Alternatively, the device may be coated in silver Hydrogel to achieve the same effect. Silver coating may be applied via deposition in a vacuum chamber.

Although many of the embodiments described have been illustrated using a shape memory material that is activated by a temperature change to return to its heat set shape, it should be understood that the super-elastic properties of a shape memory material could also be used. For example, a shape-memory ventilation tube that would return to its heat set shape at a temperature lower than body temperature could be restrained within a sheath and the super-elastic properties would allow it to return to its undeformed state upon deployment.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claim.

What is claimed is:

1. An insertion system that inserts an ear tube having a distal end and a proximal end into a tympanic membrane, the insertion system comprising:
   a handle;
   a rod member longitudinally extending from the handle and including a distal end, wherein the rod member is longitudinally stationary relative to the handle;
   a hollow sheath member including a distal end having a cutting edge, a proximal end and a slot extending from a first end located at the cutting edge of the hollow sheath member to a second end located between the cutting edge and the proximal end of the hollow sheath member, wherein the hollow sheath member surrounds the distal end of the rod member and at least partially surrounds the ear tube;
   wherein the distal end of the rod member is adjacent the proximal end of the ear tube; and
   wherein the rod member is stationary relative to the handle when the ear tube is being inserted into the tympanic membrane.

2. The insertion system of claim 1, wherein the distal end of the sheath member is tapered such that a first side of the sheath member has a length that is greater than a second side opposing the first side of the sheath member.

3. The insertion system of claim 2, wherein the second side of the sheath member comprises the slot.

4. The insertion system of claim 1, further comprising an actuator coupled to the sheath member, wherein the actuator retracts the sheath member from around the ear tube after the cutting edge of the sheath member incises the tympanic membrane and while the rod member is kept fixed against the proximal end of the ear tube.

5. The insertion system of claim 4, further comprising a suction member configured to evacuate fluid through the incision in the tympanic membrane.

6. The insertion system of claim 1, wherein a portion of the ear tube is visible through the slot in the sheath member to provide a visual indicator.

7. The insertion system of claim 6, wherein the proximal end of the ear tube comprises a plurality of proximal members and wherein the portion of the ear tube that provides the visual indicator comprises at least one of the plurality of proximal members protruding through the slot in the sheath member.

8. An inserter that inserts an ear tube having a distal end and a proximal end into a tympanic membrane, the inserter comprising:
   a handle;
   a positioning rod longitudinally extending from the handle and terminating at a distal end, wherein the rod member is longitudinally stationary relative to the handle;
   a hollow sheath member that houses the ear tube and includes a distal cutting edge for incising the tympanic membrane, the hollow sheath member surrounding a portion of the positioning rod and the ear tube such that the distal end of the positioning rod is located adjacent the proximal end of the ear tube; and
   an actuation mechanism located on the handle and coupled to the hollow sheath member by an elongated actuation member, wherein the actuation mechanism moves the hollow sheath member relative to the ear tube and the positioning rod after the ear tube and the hollow sheath member are placed in an incision of the tympanic membrane.

9. The inserter of claim 8, wherein the positioning rod comprises a hollow positioning rod and the elongated actuation member extends within the hollow positioning rod from the actuation mechanism and through an opening in the hollow positioning rod to couple to the hollow sheath member at a coupling point on the hollow sheath member.

10. The inserter of claim 8, wherein the hollow sheath member comprises a slot extending from a first end located at the distal cutting edge of the hollow sheath member to a second end located between the distal end and a proximal end of the hollow sheath member.

11. The inserter of claim 10, wherein a portion of the ear tube is visible through the slot in the hollow sheath member to provide a visual indicator.

12. The inserter of claim 11, wherein the proximal end of the ear tube comprises a plurality of proximal members, wherein the portion of the ear tube that provides the visual indicator comprises at least one of the plurality of proximal members protruding through the slot in the hollow sheath member.

13. A method of inserting an ear tube into a tympanic membrane, the method comprising:
   obtaining an inserter including a handle, a rod member that has a distal end and a sheath member that surrounds the distal end of the rod member and has a cutting edge, wherein the sheath member includes a slot extending from a first end located at the cutting edge of the sheath member to a second end located between the cutting edge and a proximal end of the sheath member;
   loading the ear tube into the sheath member such that the distal end of the rod member is adjacent a proximal end of the ear tube and a portion of the ear tube protrudes through the slot in the sheath member;
   inserting the sheath member and a portion of the rod member, which is stationary relative to the handle, into an ear canal to a depth that allows the cutting edge of the sheath member to make an incision in the tympanic membrane and a portion of the ear tube to be located through the incision;
   retracting the sheath member while the distal end of the rod member remains fixed adjacent to the proximal end of the ear tube that is partially located through the incision; and
   removing the rod member and the sheath member from the ear canal such that the ear tube is left in the incision; and
   wherein the portion of the ear tube that protrudes through the slot in the sheath member remains visible to a user of the inserter during the steps of inserting the sheath member and the portion of the rod member into the ear canal, retracting the sheath member and removing the rod member and the sheath member from the ear canal.

14. The method of claim 13, wherein retracting the sheath member comprises retracting the sheath member using a flexible actuation member that couples an actuation device to the sheath member.

15. The method of claim 13, wherein inserting the sheath member and the portion of the rod member to a depth where a portion of the ear tube is located in the incision comprises inserting the sheath member and the portion of the rod member such that a visual indicator on the ear tube remains visible.

16. The method of claim 13, wherein the ear tube comprises a proximal end having a plurality of proximal members, wherein the portion of the ear tube that protrudes through the slot in the sheath member to provide the visual indicator comprises one of the proximal members.

* * * * *